US010267873B2

(12) United States Patent
Gleich et al.

(10) Patent No.: US 10,267,873 B2
(45) Date of Patent: Apr. 23, 2019

(54) COMBINED MPI AND MRI APPARATUS AND METHOD FOR INFLUENCING AND/OR DETECTING MAGNETIC PARTICLES

(75) Inventors: Bernhard Gleich, Hamburg (DE); Juergen Erwin Rahmer, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 1737 days.

(21) Appl. No.: 13/988,862

(22) PCT Filed: Nov. 29, 2011

(86) PCT No.: PCT/IB2011/055353
§ 371 (c)(1),
(2), (4) Date: May 22, 2013

(87) PCT Pub. No.: WO2012/077015
PCT Pub. Date: Jun. 14, 2012

(65) Prior Publication Data

US 2013/0241548 A1 Sep. 19, 2013

(30) Foreign Application Priority Data

Dec. 10, 2010 (EP) .................................... 10194492

(51) Int. Cl.
*G01R 33/28* (2006.01)
*G01R 33/44* (2006.01)
(Continued)

(52) U.S. Cl.
CPC ............ *G01R 33/28* (2013.01); *A61B 5/0515* (2013.01); *G01R 33/1276* (2013.01); *G01R 33/44* (2013.01)

(58) Field of Classification Search
USPC .......................... 324/300–322; 600/407–435
See application file for complete search history.

(56) References Cited

U.S. PATENT DOCUMENTS 8,350,566 B2 * 1/2013 Ohyu ....................... A61B 5/05 324/300
8,666,473 B2 * 3/2014 Gleich ................. A61B 5/0515 600/409
(Continued)

FOREIGN PATENT DOCUMENTS

DE 10151778 5/2003
EP 1304542 4/2003
(Continued)

OTHER PUBLICATIONS

I. Schmale et al., "An introduction to the Hardware of Magnetic Particle Imaging", Jan. 1, 2009, World Congress on Medical Physics and Biomedical Engineering: Sep. 7-12, 2009, Munich, Germany; WC 2009; 11th International Congress of the IUPESM, pp. 450-453.

*Primary Examiner* — Melissa Koval
*Assistant Examiner* — Tiffany Fetzner

(57) ABSTRACT

An apparatus for operation in a magnetic particle imaging mode for influencing and/or detecting magnetic particles in a field of view, and for operation in a magnetic resonance imaging mode, includes a selector having a selection field signal generator and selection field coils, a driver having a drive field signal generator and drive field coils for changing the position in space of the two sub-zones in the field of view by a magnetic drive field so that the magnetization of magnetic particles changes locally, and a focuser having a focus field signal generator and a focus field coil unit for changing the position in space of the field of view by a magnetic focus field. The focus field coil unit includes at least six focus field coils arranged for generating magnetic focus field components in different directions, where a first set of at least three focus field coils is arranged on a first side of the field of view and a second set of at least three focus (Continued)

field coils is arranged on a second side of the field of view opposite said first side.

15 Claims, 21 Drawing Sheets

(51) Int. Cl.
*A61B 5/05* (2006.01)
*G01R 33/12* (2006.01)

(56) References Cited

U.S. PATENT DOCUMENTS

| | | | | |
|---|---|---|---|---|
| 8,981,770 | B2 * | 3/2015 | Gleich | A61B 5/05 324/214 |
| 9,008,749 | B2 * | 4/2015 | Buzug | A61B 5/05 600/409 |
| 9,044,160 | B2 * | 6/2015 | Knopp | A61B 5/0515 |
| 2008/0309330 | A1 * | 12/2008 | Ohyu | A61B 5/05 324/232 |
| 2011/0251476 | A1 | 10/2011 | Gleich et al. | |
| 2012/0119739 | A1 * | 5/2012 | Gleich | A61B 5/05 324/309 |
| 2012/0126808 | A1 * | 5/2012 | Knopp | A61B 5/0515 324/301 |
| 2012/0146632 | A1 * | 6/2012 | Gleich | A61B 5/05 324/214 |
| 2012/0310076 | A1 * | 12/2012 | Buzug | A61B 5/05 600/409 |
| 2013/0241548 | A1 * | 9/2013 | Gleich | A61B 5/0515 324/307 |
| 2017/0354344 | A1 * | 12/2017 | Schmale | A61B 5/0515 |

FOREIGN PATENT DOCUMENTS

| | | |
|---|---|---|
| JP | 2008000324 A | 1/2008 |
| WO | WO2004091386 | 10/2004 |
| WO | WO2004091390 | 10/2004 |
| WO | WO2004091394 | 10/2004 |
| WO | WO2004091395 | 10/2004 |
| WO | WO2004091396 | 10/2004 |
| WO | WO2004091397 | 10/2004 |
| WO | WO2004091398 | 10/2004 |
| WO | WO2004091408 | 10/2004 |
| WO | 2010125510 A1 | 11/2010 |

* cited by examiner

COMBINED MPI AND MRI APPARATUS AND METHOD FOR INFLUENCING AND/OR DETECTING MAGNETIC PARTICLES

FIELD OF THE INVENTION

The present invention relates to an apparatus and a method for operation in a magnetic particle imaging mode for influencing and/or detecting magnetic particles in a field of view and for operation in a magnetic resonance imaging mode. Further, the present invention relates to a computer program for implementing said method on a computer and for controlling such an apparatus. The present invention relates particularly to the field of Magnetic Particle Imaging (MPI) and Magnetic Resonance Imaging (MRI).

BACKGROUND OF THE INVENTION

Magnetic Particle Imaging (MPI) is an emerging medical imaging modality. The first versions of MPI were two-dimensional in that they produced two-dimensional images. Newer versions are three-dimensional (3D). A four-dimensional image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MP image of an object's volume of interest is generated in two steps. The first step, referred to as data acquisition, is performed using an MPI scanner. The MPI scanner has means to generate a static magnetic gradient field, called the "selection field", which has a (single) field-free point (FFP) at the isocenter of the scanner (or, in other embodiments, a field-free line in the central area of the scanner). Moreover, this FFP is surrounded by a first sub-zone with a low magnetic field strength, which is in turn surrounded by a second sub-zone with a higher magnetic field strength. In addition, the scanner has means to generate a time-dependent, spatially nearly homogeneous magnetic field. Actually, this field is obtained by superposing a rapidly changing field with a small amplitude, called the "drive field", and a slowly varying field with a large amplitude, called the "focus field". By adding the time-dependent drive and focus fields to the static selection field, the FFP may be moved along a predetermined FFP trajectory throughout a "volume of scanning" surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles; if the object is an animal or a patient, a contrast agent containing such particles is administered to the animal or patient prior to the scan. During the data acquisition, the MPI scanner moves the FFP along a deliberately chosen trajectory that traces out/covers the volume of scanning, or at least the field of view. The magnetic nanoparticles within the object experience a changing magnetic field and respond by changing their magnetization. The changing magnetization of the nanoparticles induces a time-dependent voltage in each of the receive coils. This voltage is sampled in a receiver associated with the receive coil. The samples output by the receivers are recorded and constitute the acquired data. The parameters that control the details of the data acquisition make up the "scan protocol".

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model can be formulated as an integral operator that acts on the acquired data; the reconstruction algorithm tries to undo, to the extent possible, the action of the model.

Such an MPI apparatus and method have the advantage that they can be used to examine arbitrary examination objects—e.g. human bodies—in a non-destructive manner and with a high spatial resolution, both close to the surface and remote from the surface of the examination object. Such an apparatus and method are generally known and have been first described in DE 101 51 778 A1 and in Gleich, B. and Weizenecker, J. (2005), "Tomographic imaging using the nonlinear response of magnetic particles" in Nature, vol. 435, pp. 1214-1217, in which also the reconstruction principle is generally described. The apparatus and method for magnetic particle imaging (MPI) described in that publication take advantage of the non-linear magnetization curve of small magnetic particles.

Compared to an MRI scanner, in an MPI scanner the magnetic gradient field (i.e. the magnetic selection field) is generated with a spatial distribution of the magnetic field strength such that the field of view comprises a first sub-area with lower magnetic field strength (e.g. the FFP), the lower magnetic field strength being adapted such that the magnetization of the magnetic particles located in the first sub-area is not saturated, and a second sub-area with a higher magnetic field strength, the higher magnetic field strength being adapted such that the magnetization of the magnetic particles located in the second sub-area is saturated. Due to the non-linearity of the magnetization characteristic curve of the magnetic particles the magnetization and thereby the magnetic field generated by the magnetic particles shows higher harmonics, which, for example, can be detected by a detection coil. The evaluated signals (the higher harmonics of the signals) contain information about the spatial distribution of the magnetic particles, which again can be used e.g. for medical imaging, for the visualization of the spatial distribution of the magnetic particles and/or for other applications.

Thus, an MPI apparatus and method are based on a new physical principle (i.e. the principle referred to as MPI) that is different from other known conventional medical imaging techniques, as for example local magnetic resonance (LMR) or nuclear magnetic resonance (NMR). In particular, this new MPI-principle, does, in contrast to LMR and NMR, not exploit the influence of the material on the magnetic resonance characteristics of protons, but rather directly detects the magnetization of the magnetic material by exploiting the non-linearity of the magnetization characteristic curve. In particular, the MPI-technique exploits the higher harmonics of the generated magnetic signals which result from the non-linearity of the magnetization characteristic curve in the area where the magnetization changes from the non-saturated to the saturated state.

As explained above MPI delivers 3D images of magnetic particle distributions. For an anatomical reference, MRI using an MPI scanner is highly desirable, which would be greatly simplified, if standard gradient encoding schemes could be applied.

SUMMARY OF THE INVENTION

It is an object of the present invention to provide an apparatus and a method for operation in a magnetic particle imaging mode for influencing and/or detecting magnetic particles in a field of view and for operation in a magnetic resonance imaging mode. It is a further object of the present invention to provide a corresponding computer program for implementing said method.

In a first aspect of the present invention an apparatus for operation in a magnetic particle imaging mode for influencing and/or detecting magnetic particles in a field of view and for operation in a magnetic resonance imaging mode is presented comprising:

- selection means comprising a selection field signal generator unit and selection field coils for generating a magnetic selection field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view,
- drive means comprising a drive field signal generator unit and a drive field coils for changing the position in space of the two sub-zones in the field of view by means of a magnetic drive field so that the magnetization of the magnetic material changes locally, and
- focus means comprising a focus field signal generator unit and a focus field coil unit for changing the position in space of the field of view by means of a magnetic focus field, wherein said focus field coil unit comprises at least six focus field coils arranged for generating magnetic focus field components in different directions, wherein a first set of at least three focus field coils is arranged on a first side of the field of view and a second set of at least three focus field coils is arranged on a second side of the field of view opposite said first side.

In an aspect of the present invention a corresponding method is presented for operating such an apparatus, said method comprising the steps of:

i) for operating the apparatus in a magnetic particle imaging mode,

- providing two focus field coils of different sets oppositely arranged on different sides of the field of view with focus field currents of opposite directions for generating a substantially homogeneous magnetic focus field between the focus field coils, and
- providing the selection field coils with selection field currents for generating said magnetic selection field, ii) for operating the apparatus in a magnetic resonance imaging mode,

- providing two focus field coils of different sets oppositely arranged on different sides of the field of view with gradient field currents of identical directions for generating a gradient magnetic field between the focus field coils, and
- providing the selection field coils with homogenous field currents for generating either a homogenous stationary magnetic field or a pre-polarizing and a bias magnetic field.

In a further aspect of the present invention another apparatus for operation in a magnetic particle imaging mode for influencing and/or detecting magnetic particles in a field of view and for operation in a magnetic resonance imaging mode is presented comprising:

- selection means comprising a selection field signal generator unit and selection field elements for generating a magnetic selection field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view,
- drive means comprising a drive field signal generator unit and a drive field coil unit for changing the position in space of the two sub-zones in the field of view by means of a magnetic drive field so that the magnetization of the magnetic material changes locally, wherein said drive field coil unit comprises at least six drive field coils arranged for generating magnetic drive field components in different directions, wherein a first set of at least three drive field coils is arranged on a first side of the field of view and a second set of at least three focus field coils is arranged on a second side of the field of view opposite said first side.

In an aspect of the present invention a corresponding method for operating such an apparatus is presented, said method comprising the steps of:

i) for operating the apparatus in a magnetic particle imaging mode,

- providing two drive field coils of different sets oppositely arranged on different sides of the field of view with drive field currents of opposite directions for generating a substantially homogeneous magnetic drive field between the drive field coils, and
- providing the selection field coils with selection field currents for generating said magnetic selection field, ii) for operating the apparatus in a magnetic resonance imaging mode, providing two drive field coils of different sets oppositely arranged on different sides of the field of view with gradient field currents of identical directions for generating a gradient magnetic field between the drive field coils, and

- providing the selection field coils with homogenous field currents for generating either a homogenous stationary magnetic field or a pre-polarizing and a bias magnetic field.

Still further, in an aspect of the present invention a computer program is presented comprising program code means for causing a computer to control an apparatus as provided according to the present invention to carry out the steps of the method for operation as provided according to the present invention when said computer program is carried out on the computer.

Preferred embodiments of the invention are defined in the dependent claims. It shall be understood that the claimed methods and the claimed computer program have similar and/or identical preferred embodiments as the claimed apparatus and as defined in the dependent claims.

The present invention is based on the idea to replace either the focus field coils and/or the drive field coils of the conventional MPI scanner by a larger number of differently arranged focus field coils and/or drive field coils. This is done for at least two pairs of conventionally used focus field coils and/or drive field coils, i.e. two pairs of conventional focus field coils are replaced by a group of at least six focus field coils, and/or two pairs of conventional drive field coils are replaced by a group of six drive field coils. The respective coils of a set of respective three (focus field or drive field) coils are arranged on different (opposite) sides of the field of view (like the two coils of a pair in the conventional arrangement), e.g. above and below the field of view. Preferably, the coils of the two sets arranged on opposite sides of the field of view are substantially facing each other, i.e. the areas covered by the turns of the respective coils are substantially arranged opposite to each other.

In this way the desired essential magnetic fields for both an MPI mode and an MRI mode can be generated by said coils. In particular, in an MPI mode a substantially homogeneous magnetic field is generated, while in an MRI mode a gradient magnetic field is generated by those sets of focus field coils or drive field coils, respectively. Hence, the same coils can be used in both modes by just providing them with different currents, which is not possible in either a known MPI apparatus or a known MRI apparatus.

The focus field coils are also able to generate a sufficiently strong magnetic field of e.g. above 100 mT to cover a relevant field of view, which would not be possible with standard gradient coils as used in conventional MRI apparatus which could thus not simply be used as focus field coils in an MPI mode. The drive field coils are also able to generate a sufficiently strong magnetic field of e.g. above 15 mT at a frequency above 20 kHz, which would not be possible with standard gradient coils as used in conventional MRI apparatus which could thus not simply be used as drive field coils in an MPI mode.

Also the selection field coils provided in the apparatus according to the present invention can be used for generating the desired magnetic fields for both modes. In particular, in the MPI mode magnetic gradient field with a substantially field free point is generated, while in the MRI mode either a homogenous stationary magnetic field (so-called B0-field in classical MRI) or a pre-polarizing and a bias magnetic field (for pre-polarized MRI) is generated by those selection field coils.

For the generation of RF pulses and for receiving MR signals in the MRI mode various coils of the apparatus can generally be used, in particular receive coils used for receiving MPI signals in the MPI mode or the drive field coils generally used in the MPI mode to move the FFP through the field of view. Alternatively, separate coils can be provided for these purposes.

Depending on the mode in which the proposed apparatus shall be operated appropriate currents are provided to the various coils. The focus field signal generator unit and the selection field generator unit are adapted accordingly, in particular for generating the currents as required for operating the apparatus as defined above.

In a preferred embodiment the at least three focus field coils of each set of focus field coils are substantially arranged in a respective focus field coil plane layer. Here, focus field coil plane is to be understood as a kind of layer having a certain thickness that substantially corresponds to the extension of the focus field coils in a direction perpendicular to said plane. In other words, said focus field coils are substantially arranged in said plane and are not arranged in different planes and/or displaced with different distances from said plane. This arrangement provides a simple mechanical arrangement of the focus field coils and enables to easier calculate/predict the magnetic field generated by said focus field coils.

According to another embodiment respective two focus field coils of different sets form a pair of focus field coils having substantially the same symmetry axis, wherein the symmetry axes of the different pairs are arranged substantially in parallel to each other arranged at different positions with respect to the field of view. The at least three focus field coils of the respective sets are, for instance, substantially arranged at the three corners of an equal-sided triangle, i.e. are arranged on a regular grid which further facilitates calculating/predicting the generated magnetic field. In case of four focus field coils in each set, they may, for instance, be arranged at the four corners of a rectangle.

Preferably, in an embodiment said focus field coil unit comprises at least eight focus field coils, said eight focus field coils being assigned to two focus field coil sub-units each comprising two pairs of focus field coils, said eight focus field coils of said two focus field coil sub-units being arranged on different sides of the field of view, wherein two respective coils of each of the four pairs are substantially facing each other. This enables, in the MRI mode, the generation of magnetic gradient fields in two directions and, in the MPI mode, the generation of homogeneous magnetic fields in two different directions. The embodiment is based on the idea to split either the focus field coils and/or the drive field coils of the conventional MPI scanner into pairs of focus field coils and/or drive field coils. This is done for at least one pair of conventionally used focus field coils and/or drive field coils, i.e. one pair of conventional focus field coils is replaced by a group of four focus field coils (called "focus field coil subunit" hereinafter), and/or one pair of conventional drive field coils is replaced by a group of four drive field coils (called "drive field coil subunit" hereinafter). The respective coils of a group ("subunit") are arranged on different sides of the field of view (like the two coils of a pair in the conventional arrangement), and are further arranged such that two coils arranged on opposite sides of the field of view are substantially facing each other, i.e. the areas covered by the turns of the respective coils are substantially arranged opposite to each other.

Consequently, a method of operating such an embodiment of the apparatus comprises the steps of:

i) for operating the apparatus in a magnetic particle imaging mode,
- providing two drive field coils of different sets oppositely arranged on different sides of the field of view with drive field currents of opposite directions for generating a substantially homogeneous magnetic drive field between the drive field coils, and
- providing the selection field coils with selection field currents for generating said magnetic selection field, ii) for operating the apparatus in a magnetic resonance imaging mode,
- providing two drive field coils of different sets oppositely arranged on different sides of the field of view with gradient field currents of identical directions for generating a gradient magnetic field between the drive field coils, and
- providing the selection field coils with homogenous field currents for generating either a homogenous stationary magnetic field or a pre-polarizing and a bias magnetic field.

Accordingly, in an embodiment in which such an apparatus shall be operated in an MPI mode the focus field signal generator unit is adapted for providing the two focus field coils of each pair of focus field coils of said focus field coil subunit with focus field currents of opposite directions for generating a substantially homogeneous magnetic focus field between the focus field coils and the selection field generator unit is adapted for providing the selection field coils with selection field currents for generating said magnetic selection field. Further, when the apparatus shall be operated in an MRI mode the focus field signal generator unit is adapted for providing the two focus field coils of said pairs of focus field coils of said focus field coil subunit with gradient field currents of the same direction, wherein the two focus field coils of a first pair are provided with the gradient field current of a different direction than the two focus field coils of the second pair, for generating a gradient magnetic focus field between the focus field coils. Further, in this embodiment the selection field generator unit is adapted for providing the selection field coils with homogeneous field currents for generating either a homogeneous stationary magnetic field for classic MRI or a pre-polarizing magnetic field (and, preferably, a bias magnetic field) for pre-polarized MRI.

Said four focus field coils of each two pairs of focus field coils are substantially arranged in a respective focus field coil layer, wherein said two respective focus field coil layers are substantially arranged orthogonal to each other in a preferred embodiment. As explained above, such a regular arrangement of the focus field coils allows to easier calculate/predict the generated magnetic fields. Further, the mechanical arrangement of the focus field coils is facilitated.

Still further, in an embodiment the two respective focus field coils of each of said two focus field coil subunits are arranged in a respective focus field coil plane, wherein said two respective focus field coil planes are arranged substantially in parallel to each other on different sides of the field of view. Thus, in a first focus field coil plane two focus field coils of a first subunit and two focus field coils of a second subunit are arranged, while the other four focus field coils are arranged in another focus field coil plane. Preferably, these two focus field coil planes are arranged perpendicular to said two respective focus field coil layers (each layer preferably comprising, as explained above, all four focus field coils of a subunit).

For instance, if the four focus field coils of a first focus field coil subunit are arranged in a focus field coil layer parallel to the x-z-plane (of a Cartesian coordinate system), and the four focus field coils of a second subunit are arranged in a focus field coil layer parallel to the y-z-plane, the two focus field coil planes of this embodiment are arranged parallel to the x-y-plane. Thus, preferably, a very regular arrangement of all focus field coils is achieved according to this embodiment.

Advantageously, a third focus field coil subunit is provided comprising one pair of focus field coils, said two focus field coils substantially facing each other. While generally also the selection field coils can be used as third focus field coil subunit for generating a homogeneous field in a third direction, separate focus field coils are preferably provided for this purpose in this embodiment. These focus field coils are preferably arranged substantially in parallel to the two respective focus field coil planes referred to above. As an alternative, of course, also the third focus field coil unit may comprise four focus field coils quite similarly to the other focus field coil subunits explained above. These four focus field coils of a third focus field coil subunit would then be arranged in a focus field coil layer arranged orthogonal to the other focus field coil layers in which the focus field coils of the first and second subunits are arranged.

For the form of the focus field coils different embodiments are usable. In particular, just to give a few examples, the focus field coils may be arranged in the form of ring coils, e.g. having a circular form, wound around a common axis. The windings may be arranged circularly or spirally on a common plane or may be arranged in the form of a solenoid. Preferably, in an embodiment the focus field coils have a substantially D-shaped form, wherein the straight arm of respective two focus field coils of different pairs are adjacent to each other (but separated by a short distance). In this way they can be arranged close to each other and are able to generate a well homogeneous magnetic field in its central area between the focus field coils.

Still further, in an embodiment the apparatus comprises receiving means comprising at least one signal receiving unit and at least one receiving coil for acquiring detection signals, which detection signals depend on the magnetization in the field of view, which magnetization is influenced by the change in the position and space of the first and second sub-zone. By use of the detection signals, for instance, information of the local distribution of the magnetic particles in the field of view can be obtained which can be used to derive anatomical information of a patient's body portion located in the field of view.

In the above various embodiments have been explained particularly for the arrangement and form of focus field coils. Similar or even identical embodiments exist for the arrangement and form of drive field coils if, instead or in addition to the focus field coils, the drive field coils are provided and arranged as explained above in an aspect of the present invention. Simply said, in the above explained embodiments the term "focus field" can be replaced by "drive field" to understand the various embodiments that exist for an apparatus making use of the above explained idea by modifying the type, number and/or arrangement of drive field coils compared to the known apparatus rather than or in addition to modifying the type, number and/or arrangement of focus field coils.

In a preferred embodiment said drive field coil unit comprises three drive field coil subunits, wherein at least one drive field coil subunit comprises one pair of drive field coils arranged for generating a magnetic drive field component in a first direction, and wherein the other two drive field coil subunits together comprise said at least six drive field coils arranged for generating magnetic drive field components in two further directions.

Consequently, a method of operating such an embodiment of the apparatus comprises the steps of:

i) for operating the apparatus in a magnetic particle imaging mode, providing the two drive field coils of each pair of drive field coils of said drive field coil subunit with drive field currents of opposite directions for generating a substantially homogeneous magnetic drive field between the drive field coils, and providing the selection field coils with selection field currents for generating said magnetic selection field, ii) for operating the apparatus in a magnetic resonance imaging mode, providing the two drive field coils of said pair of drive field coils of said drive field coil subunit with gradient field currents of the same direction, wherein the two drive field coils of a first pair are provided with a gradient field current of a different direction than the two drive field coils of the second pair, for generating a gradient magnetic field between the drive field coils, and providing the selection field coils with homogenous field currents for generating either a homogenous stationary magnetic field or a pre-polarizing and a bias magnetic field.

Further, in an embodiment the four coils of said two pairs of drive field coils of said at least one drive field coil subunit are substantially arranged in a common coil layer.

In a further embodiment each two coils of each of said two pairs of drive field coils of said at least one drive field coil subunit have substantially the same symmetry axis, wherein the symmetry axes of the two pairs are arranged substantially parallel on opposite sides of the field of view.

In a further embodiment two drive field coil subunits each comprise two pairs of drive field coils, said eight coils of said two drive field coil subunits being arranged on different sides of the field of view, two coils of each of the four pairs substantially facing each other.

In a further embodiment the four coils of each two pairs of drive field coils of said two drive field coil subunits are substantially arranged in a respective coil layer, wherein said two respective coil layers are substantially arranged perpendicular to each other.

In a further embodiment two respective coils of a each of said two drive field coil subunits are arranged in a respective coil plane, wherein said two respective coil planes are arranged substantially parallel on different sides of the field of view.

In a further embodiment said two respective coil planes are arranged perpendicular to said two respective coil layers.

In a further embodiment a third drive field coil subunit comprises a one pair of drive field coils, said two drive field coil substantially facing each other.

In a further embodiment the drive field coils of said third drive field coil subunit are arranged substantially parallel to said two respective coil planes.

In a further embodiment said drive field signal generator unit is adapted for providing the two drive field coils of each pair of drive field coils of said at least one drive field coil subunit with drive currents of opposite directions for generating a substantially homogeneous magnetic drive field between the coils of said drive field coil subunit.

said drive field signal generator unit is adapted for providing the two drive field coils of each pair of drive field coils of said at least one drive field coil subunit with drive currents of the same direction, wherein the two drive field coils of a first pair are provided with drive current of a different direction than the drive two drive field coils of the second pair, for generating a gradient magnetic drive field between the coils of said drive field coil subunit.

In an embodiment said drive field coils have a substantially D-shaped form, wherein the straight arm of respective two drive field coils of different pairs are adjacent to each other.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 4. In particular, two embodiments of an MPI scanner for medical diagnostics will be described. An informal description of the data acquisition will also be given. The similarities and differences between the two embodiments will be pointed out.

Figure 1:
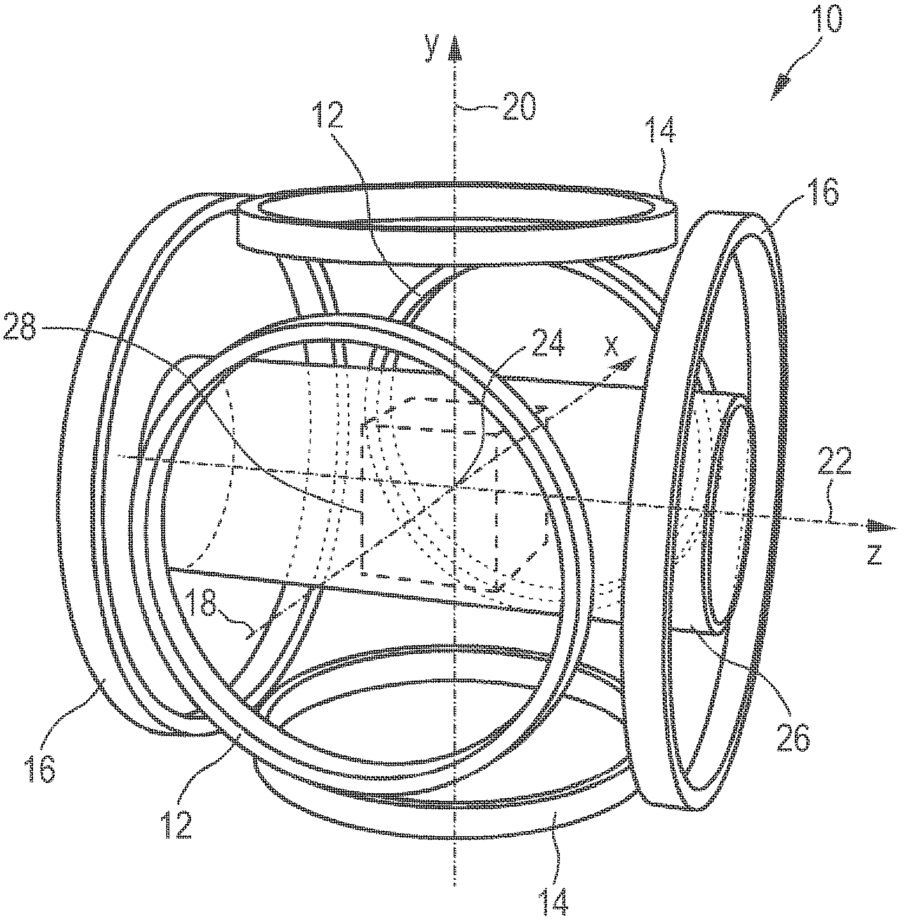
FIG. 1 shows a first embodiment of an MPI apparatus.

The first embodiment 10 of an MPI scanner shown in FIG. 1 has three pairs 12, 14, 16 of coaxial parallel circular coils, these coil pairs being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x- and z-axes are horizontal. The coil pairs 12, 14, 16 are named after their axes. For example, the y-coil pair 14 is formed by the coils at the top and the bottom of the scanner. Moreover, the coil with the positive (negative) y-coordinate is called the $y^+$-coil ($y^-$-coil), and similarly for the remaining coils. When more convenient, the coordinate axes and the coils shall be labeled with $x_1$, $x_2$, and $x_3$, rather than with x, y, and z.

The scanner 10 can be set to direct a predetermined, time-dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the $z^+$-coil, and the current $-I^S$ is made to flow through the $z^-$-coil. The z-coil pair 16 then acts as an anti-parallel circular coil pair.

It should be noted here that the arrangement of the axes and the nomenclature given to the axes in this embodiment is just an example and might also be different in other embodiments. For instance, in practical embodiments the vertical axis is often considered as the z-axis rather than the y-axis as in the present embodiment. This, however, does not generally change the function and operation of the device and the effect of the present invention.

Figure 2:
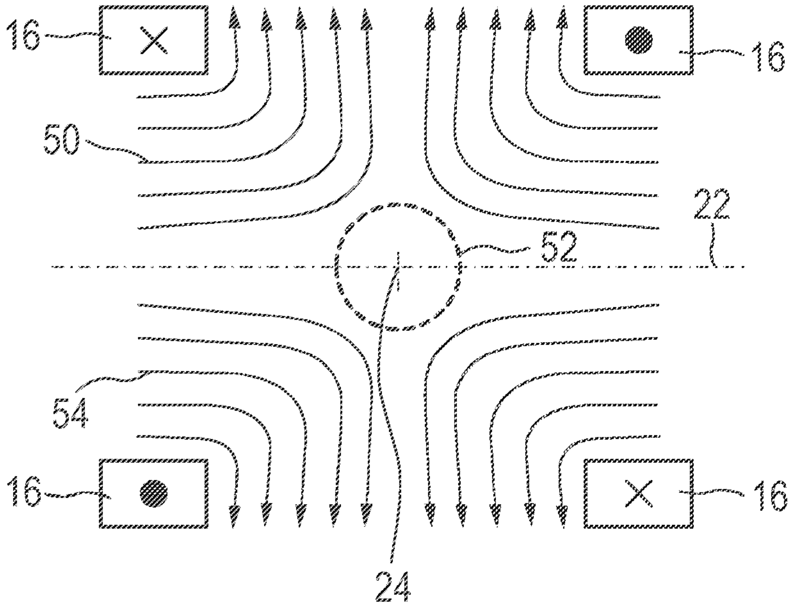
FIG. 2 shows an example of the selection field pattern produced by an apparatus as shown in FIG. 1.

The magnetic selection field, which is generally a magnetic gradient field, is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 (including the field-free point) within the field of view 28 the (overall) magnetization in the field of view 28 changes. By determining the magnetization in the field of view 28 or physical parameters influenced by the magnetization, information about the spatial distribution of the magnetic particles in the field of view 28 can be obtained. In order to change the relative spatial position of the two sub-zones 52, 54 (including the field-free point) in the field of view 28, further magnetic fields, i.e. the magnetic drive field, and, if applicable, the magnetic focus field, are superposed to the selection field 50.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field (of course, in other embodiments, separate coils may be provided). The current flowing through the $z^{\pm}$-coil is $I^D_3+I^F_3\pm I^S$. The current flowing through the remaining two coil pairs 12, 14 is $I^D_k+I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field-free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time-dependent. The difference between the focus field and the drive field is that the focus field varies slowly in time and may have a large amplitude, while the drive field varies rapidly and has a small amplitude. There are physical and biomedical reasons to treat these fields differently. A rapidly varying field with a large amplitude would be difficult to generate and potentially hazardous to a patient.

In a practical embodiment the FFP can be considered as a mathematical point, at which the magnetic field is assumed to be zero. The magnetic field strength increases with increasing distance from the FFP, wherein the increase rate might be different for different directions (depending e.g. on the particular layout of the device). As long as the magnetic field strength is below the field strength required for bringing a magnetic particle into the state of saturation, the particle actively contributes to the signal generation of the signal measured by the device; otherwise, the particle is saturated and does not generate any signal.

The embodiment 10 of the MPI scanner has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair. The receive coils are supposed to be well decoupled. The time-dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from zero Hertz ("DC") up to the frequency where the expected signal level drops below the noise level.

The embodiment 10 of the MPI scanner shown in FIG. 1 has a cylindrical bore 26 along the z-axis 22, i.e. along the axis of the selection field. All coils are placed outside this bore 26. For the data acquisition, the patient (or object) to be imaged is placed in the bore 26 such that the patient's volume of interest—that volume of the patient (or object) that shall be imaged—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, a cylinder or an arbitrary shape. A cubical field of view 28 is illustrated in FIG. 1.

The size of the first sub-zone 52 is dependent on the strength of the gradient of the magnetic selection field and on the field strength of the magnetic field required for saturation, which in turn depends on the magnetic particles. For a sufficient saturation of typical magnetic particles at a magnetic field strength of 80 A/m and a gradient (in a given space direction) of the field strength of the magnetic selection field amounting to $50\times10^3$ A/m$^2$, the first sub-zone 52 in which the magnetization of the particles is not saturated has dimensions of about 1 mm (in the given space direction).

The patient's volume of interest is supposed to contain magnetic nanoparticles. Prior to the diagnostic imaging of, for example, a tumor, the magnetic particles are brought to the volume of interest, e.g. by means of a liquid comprising the magnetic particles which is injected into the body of the patient (object) or otherwise administered, e.g. orally, to the patient.

Generally, various ways for bringing the magnetic particles into the field of view exist. In particular, in case of a patient into whose body the magnetic particles are to be introduced, the magnetic particles can be administered by use of surgical and non-surgical methods, and there are both methods which require an expert (like a medical practitioner) and methods which do not require an expert, e.g. can be carried out by laypersons or persons of ordinary skill or the patient himself/herself. Among the surgical methods there are potentially non-risky and/or safe routine interventions, e.g. involving an invasive step like an injection of a contrast agent into a blood vessel (if such an injection is at all to be considered as a surgical method), i.e. interventions which do not require considerable professional medical expertise to be carried out and which do not involve serious health risks. Further, non-surgical methods like swallowing or inhalation can be applied.

Generally, the magnetic particles are pre-delivered or pre-administered before the actual steps of data acquisition are carried out. In embodiments, it is, however, also possible that further magnetic particles are delivered/administered into the field of view.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 μm with such magnetic particles, a magnetic field of approximately 800 A/m (corresponding approximately to a flux density of 1 mT) is then required, whereas in the case of a diameter of 100 μm a magnetic field of 80 A/m suffices. Even smaller values are obtained when a coating of a material having a lower saturation magnetization is chosen or when the thickness of the layer is reduced.

In practice, magnetic particles commercially available under the trade name Resovist (or similar magnetic particles) are often used, which have a core of magnetic material or are formed as a massive sphere and which have a diameter in the range of nanometers, e.g. 40 or 60 nm.

For further details of the generally usable magnetic particles and particle compositions, the corresponding parts of EP 1304542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

During the data acquisition, the x-, y-, and z-coil pairs 12, 14, 16 generate a position- and time-dependent magnetic field, the applied field. This is achieved by directing suitable currents through the field generating coils. In effect, the drive and focus fields push the selection field around such that the FFP moves along a preselected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time-dependent voltage $V_k$ across the terminals of the receive coil pair along the $x_k$-axis. The associated receiver converts this voltage to a signal $S_k$, which it processes further.

Figure 3:
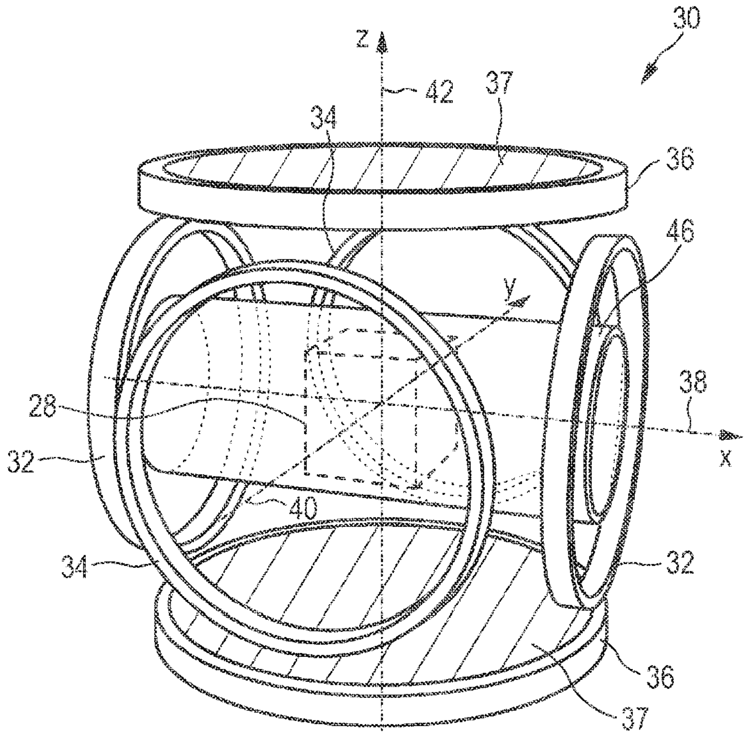
FIG. 3 shows a second embodiment of an MPI apparatus.

Like the first embodiment 10 shown in FIG. 1, the second embodiment 30 of the MPI scanner shown in FIG. 3 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The drive field is generated by a solenoid (not shown) along the x-axis 38 and by pairs of saddle coils (not shown) along the two remaining axes 40, 42. These coils are wound around a tube which forms the bore. The drive field coils also serve as receive coils.

To give a few typical parameters of such an embodiment: The z-gradient of the selection field, G, has a strength of $G/\mu_0$=2.5 T/m, where $\mu_0$ is the vacuum permeability. The temporal frequency spectrum of the drive field is concentrated in a narrow band around 25 kHz (up to approximately 150 kHz). The useful frequency spectrum of the received signals lies between 50 kHz and 1 MHz (eventually up to approximately 15 MHz). The bore has a diameter of 120 mm. The biggest cube 28 that fits into the bore 46 has an edge length of 120 mm/$\sqrt{2}\approx$84 mm.

Since the construction of field generating coils is generally known in the art, e.g. from the field of magnetic resonance imaging, this subject need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

Figure 4:
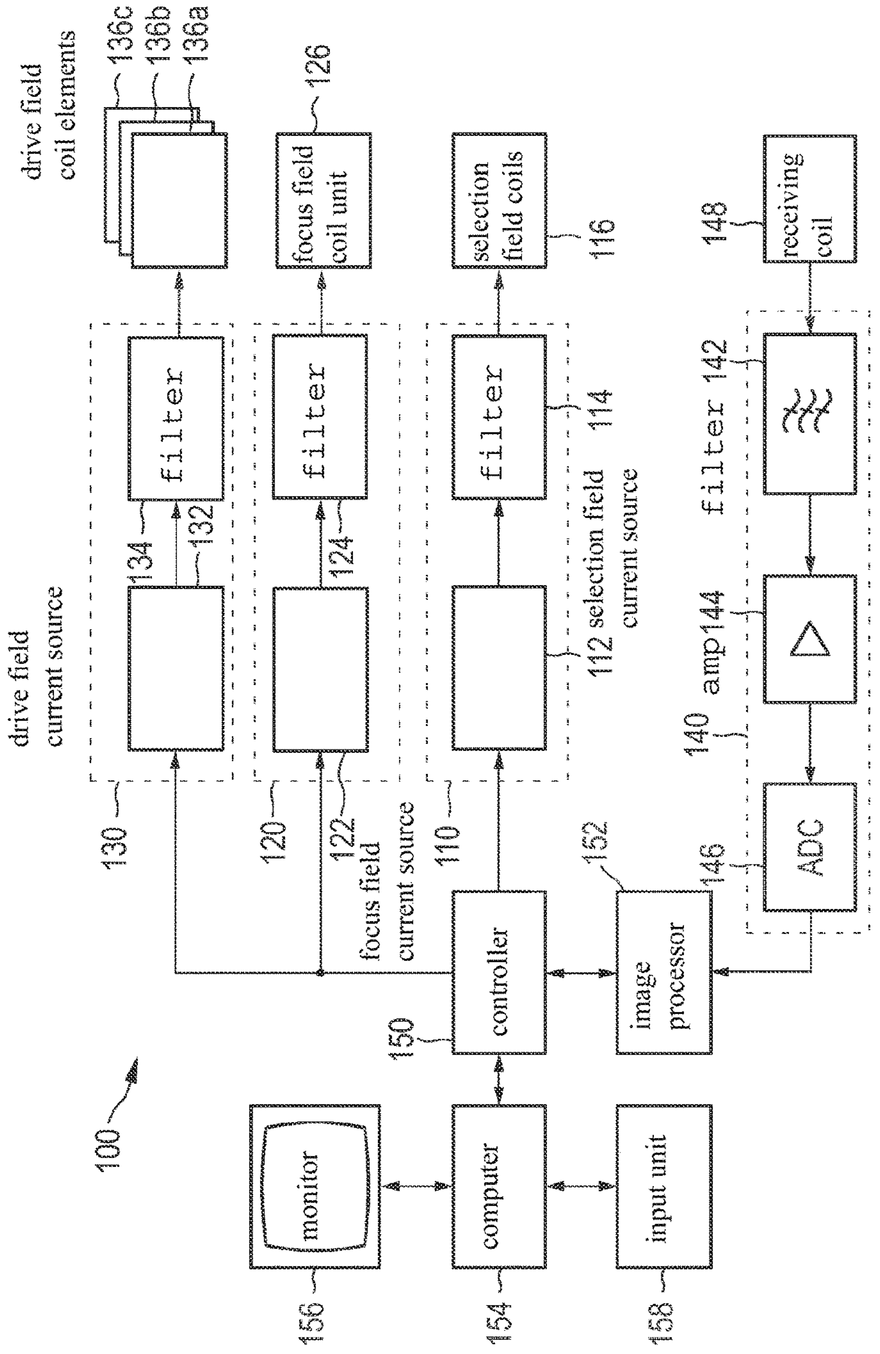
FIG. 4 shows a block diagram of an apparatus according to the present invention.

FIG. 4 shows a general block diagram of an MPI apparatus 100 according to the present invention. The general principles of magnetic particle imaging explained above are valid and applicable to this embodiment as well, unless otherwise specified.

The embodiment of the apparatus 100 shown in FIG. 4 comprises various sets of coils for generating the desired magnetic fields. First, the coils and their functions in MPI shall be explained.

For generating the magnetic selection field explained above, selection means are provided comprising a set of selection field coils 116, preferably comprising at least one pair of coil elements. The selection means further comprises a selection field signal generator unit 110. Preferably, a separate generator subunit is provided for each coil element (or each pair of coil elements) of the set 116 of selection field coils. Said selection field signal generator unit 110 comprises a controllable selection field current source 112 (generally including an amplifier) and a filter unit 114 which provide the respective section field coil element with the selection field current to individually set the gradient strength of the selection field. However, since the selection field is generally static, the filter unit 114 can also be omitted. Preferably, a constant current is provided. If the selection field coil elements are arranged as opposite coils, e.g. on opposite sides of the field of view, the selection field currents of the opposite coils are preferably oppositely oriented.

The selection field signal generator unit 110 can be controlled by a control unit 150, which preferably controls the selection field current generation 110 such that the sum of the field strength and the sum of the gradient strength of all spatial fractions of the selection field is maintained at a predefined level. For this purpose the control unit 150 can also be provided with control instructions by a user according to the desired application of the MPI apparatus, which, however, is preferably omitted according to the present invention.

For the generation of a magnetic focus field the apparatus 100 further comprises focus means comprising a set of focus field coils, referred to as focus field coil unit 126. In particular, three focus field coil subunits each comprising two or more focus field coils, as will be explained below, are provided for changing the position in space of the first and second sub-zones, in particular for changing the position in space of the field of view 28 by means of a magnetic focus field. The focus field coils are controlled by a focus field signal generator unit 120, preferably comprising a separate focus field signal generation subunit for each focus field coil subunit or even for each coil (or at least each pair of coils) of said set of focus field coil subunits. Said focus field signal generator unit 120 comprises a focus field current source 122 (preferably comprising a current amplifier) and a filter unit 124 for providing a focus field current to the respective focus field coil that shall be used for generating the magnetic focus field. The focus field current unit 120 is also controlled by the control unit 150. With the present invention, the filter unit 124 may also be omitted.

Figure 9:
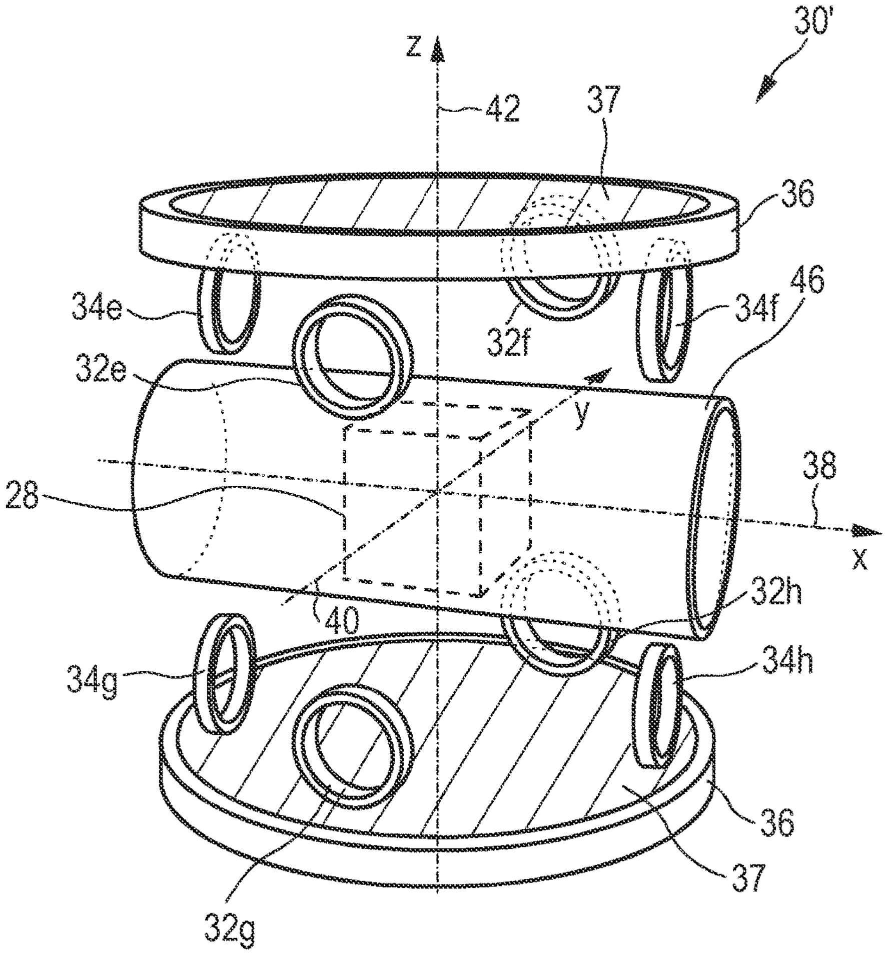
FIG. 9 shows a second embodiment of an apparatus according to the present invention.
Figure 11:
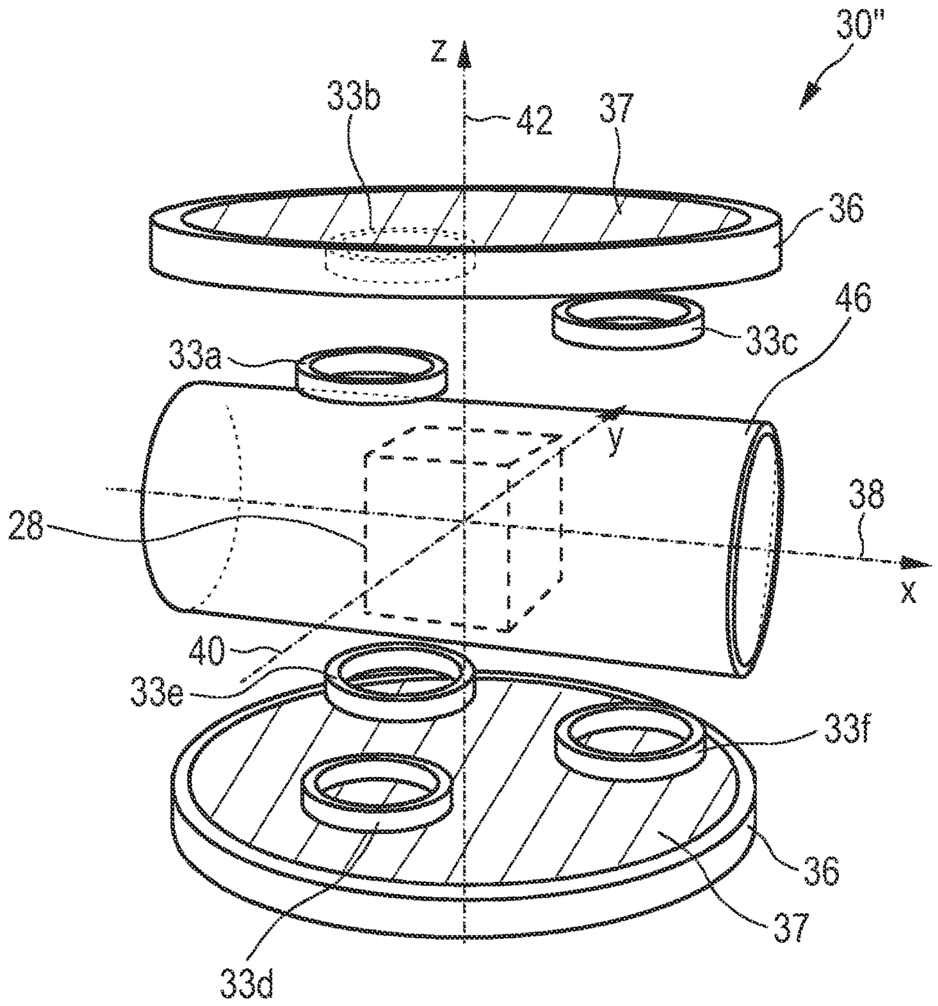
FIG. 11 shows a third embodiment of an apparatus according to the present invention.

Conventionally the focus field coil unit comprises three subunits each comprising a pair of oppositely arranged focus field coils, i.e. in a conventional MPI apparatus three pairs of oppositely arranged focus field coils are provided. In contrast, according to the present invention the focus field coil unit comprises at least six focus field coils arranged for generating magnetic focus field components in (preferably two) different directions, wherein a first set of at least three focus field coils is arranged on a first side of the field of view and a second set of at least three focus field coils is arranged on a second side of the field of view opposite said first side. Further, preferably another pair of two focus field coils (which may be identical to the selection field coils) may be provided for generating a magnetic focus field component in a third direction. More detailed and concrete embodiments showing such arrangements of coils are shown in FIGS. 6, 9 and 11 and are explained below.

For generating the magnetic drive field the apparatus 100 further comprises drive means comprising a subset of drive field coils, preferably comprising three pairs 136*a*, 136*b*, 136*c* of oppositely arranged drive field coil elements. The drive field coils are controlled by a drive field signal generator unit 130, preferably comprising a separate drive field signal generation subunit for each coil element (or at least each pair of coil elements) of said set of drive field coils. Said drive field signal generator unit 130 comprises a drive field current source 132 (preferably including a current amplifier) and a filter unit 134 (which may also be omitted with the present invention) for providing a drive field current to the respective drive field coil. The drive field current source 132 is adapted for generating a time-dependent current and is also controlled by the control unit 150.

It should be noted that in the embodiment of the apparatus 10 shown in FIG. 1 identical coils are preferably used for generating the magnetic drive field and the magnetic focus field.

For signal detection receiving means 148, in particular a receiving coil, and a signal receiving unit 140, which receives signals detected by said receiving means 148, are provided. Preferably, three receiving coils 148 and three receiving units 140—one per receiving coil—are provided in practice, but more than three receiving coils and receiving units can be also used, in which case the acquired detection signals are not 3-dimensional but K-dimensional, with K being the number of receiving coils.

Said signal receiving unit 140 comprises a filter unit 142 for filtering the received detection signals. The aim of this filtering is to separate measured values, which are caused by the magnetization in the examination area which is influenced by the change in position of the two part-regions (52, 54), from other, interfering signals. To this end, the filter unit 142 may be designed for example such that signals which have temporal frequencies that are smaller than the temporal frequencies with which the receiving coil 148 is operated, or smaller than twice these temporal frequencies, do not pass the filter unit 142. The signals are then transmitted via an amplifier unit 144 to an analog/digital converter 146 (ADC). The digitalized signals produced by the analog/digital converter 146 are fed to an image processing unit (also called reconstruction means) 152, which reconstructs the spatial distribution of the magnetic particles from these signals and the respective position which the first part-region 52 of the first magnetic field in the examination area assumed during receipt of the respective signal and which the image processing unit 152 obtains from the control unit 150. The reconstructed spatial distribution of the magnetic particles is finally transmitted via the control means 150 to a computer 154, which displays it on a monitor 156. Thus, an image can be displayed showing the distribution of magnetic particles in the field of view of the examination area.

Further, an input unit 158 may be provided, for example a keyboard. A user may therefore be able to set the desired direction of the highest resolution and in turn receives the respective image of the region of action on the monitor 156. If the critical direction, in which the highest resolution is needed, deviates from the direction set first by the user, the user can still vary the direction manually in order to produce a further image with an improved imaging resolution. This resolution improvement process can also be operated automatically by the control unit 150 and the computer 154. The control unit 150 in this embodiment sets the gradient field in a first direction which is automatically estimated or set as start value by the user. The direction of the gradient field is then varied stepwise until the resolution of the thereby received images, which are compared by the computer 154, is maximal, respectively not improved anymore. The most critical direction can therefore be found respectively adapted automatically in order to receive the highest possible resolution.

Figure 5A:
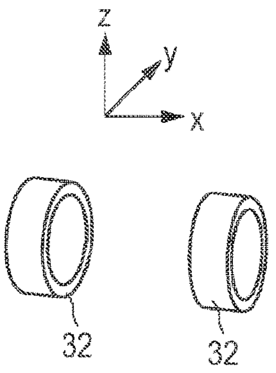
FIG. 5 shows embodiments for the arrangement of coils as proposed according to the present invention.

FIG. 5 shows separate views of a pair of conventionally used focus field coils and two embodiments of a focus field coil subunit comprising four focus field coils as proposed according to the present invention. FIG. 5*a* shows a pair of two focus field coils, for instance x focus field coils 32 as provided in the known MPI apparatus as shown in FIG. 3. These x focus field coils are conventionally used in an MPI apparatus to generate a homogeneous magnetic field in x direction.

Figure 5B:
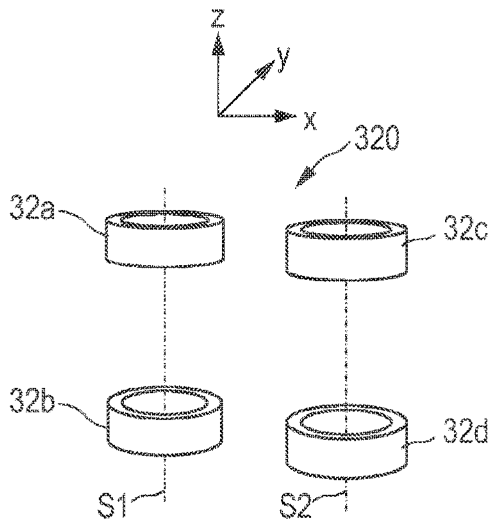
Figure 5C:
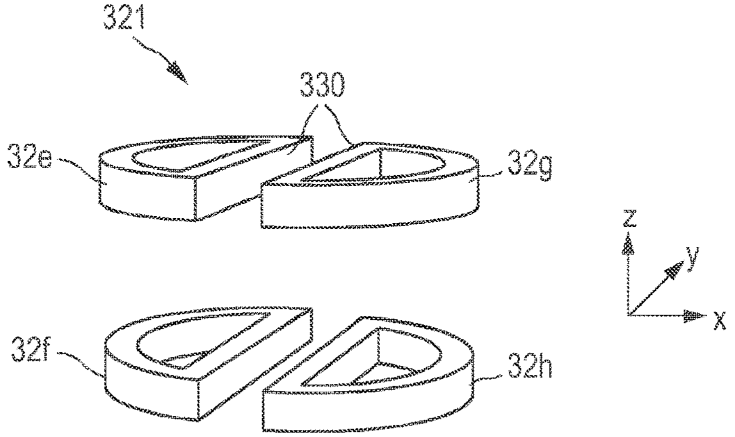

According to the present invention, this pair of x focus field coils 32 (note, it must not necessarily be the x focus field coils, but can be, in addition or alternatively, focus field coils for one or more other directions) are replaced by a focus field coil subunit comprising four coils, for which two embodiments are shown in FIGS. 5*b* and 5*c*. In the embodiment shown in FIG. 5*b* the focus field coil subunit 320 comprises four circularly wound focus field coils 32*a*, 32*b*, 32*c*, 32*d*. The field of view (not shown) is arranged between those four focus field coils. As can be seen the focus field coils 32*a*, 32*b* of a first pair are facing each other, and the focus field coils 32*c*, 32*d* of a second pair are facing each other. Further, in this embodiment, all four focus field coils 32*a*-32*d* are arranged in a common focus field coil layer, e.g.—referring to the coordinate system as used in FIG. 3—said layer being arranged parallel to the x-z-plane. Further, in this embodiment the two upper focus field coils 32*a*, 32*c* are arranged in a first focus field coil plane (parallel to the x-y-plane), and the lower focus field coils 32*b*, 32*d* are arranged in a parallel focus field coil plane. Such a regular arrangement is preferred and enables an easier mechanical arrangement of the coils and a better calculation/estimation of the generated magnetic field. However, for the present invention such a regular arrangement of the four focus field coils of a focus field coil subunit is not essential.

As further shown in FIG. 5*b* the focus field coils 32*a*, 32*b* of the first pair have a common symmetry axis 51, and the focus field coils 32*c*, 32*d* of the second pair have a common symmetry axis S2, which symmetry axes 51, S2 of the two pairs are arranged substantially in parallel to each other on opposite sides of the field of view.

Another embodiment of a focus field coil unit 321 for replacing the pair of focus field coils 32 shown in FIG. 5*a* is shown in FIG. 5*c*. Also this subunit 321 comprises four focus field coils 32*e*, 32*f*, 32*g*, 32*h*, which are arranged substantially at the same positions and the same orientations as explained for the focus field coil subunit 320 shown in FIG. 5*b*. However, in this embodiment the focus field coils 32*e*-32*h* do not have a circular form but have the form of a D, wherein the straight arms 330 of respective to neighboring focus field coils are arranged adjacent to each other as shown in FIG. 5*c*. These focus field coils 32*e*-32*h* can be easily integrated into the whole arrangement and can also be arranged between the field of view and (larger) selection field coils.

Using D-shaped coils a very compact field generator can be produced, e.g. comprising 3 layers of coils above and 3 layers of coils below the field of view. In such an embodiment, one layer contains 2 D-shaped coils for generating the x focus field, the next layer contains 2 D-shaped coils rotated by 90° for generating the z focus field, and the third layer has a single round coil for generating the y focus field and the selection field. Of course, other arrangements of the layers above each other are also possible. Thus, in general, the advantages of using D-shaped coils are a compact setup, so that the coils can be made larger, and less stored energy in the coils compared to separate coils at the same field energy.

Figure 6A:
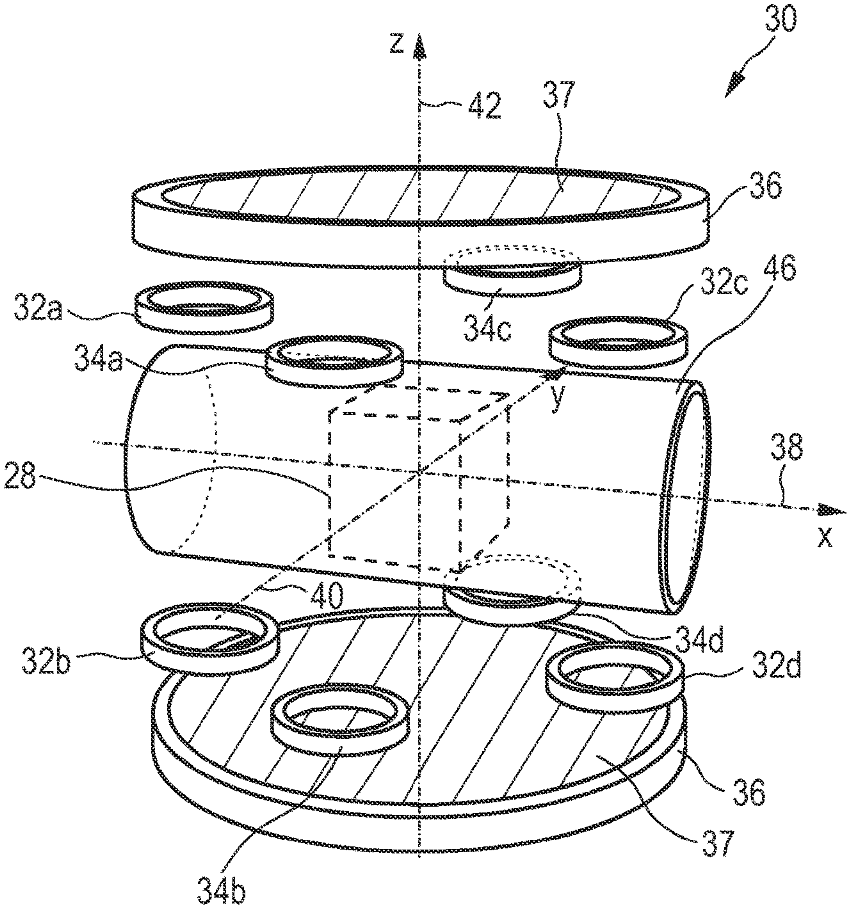
FIG. 6 shows a first embodiment of an apparatus according to the present invention.
Figure 6B:
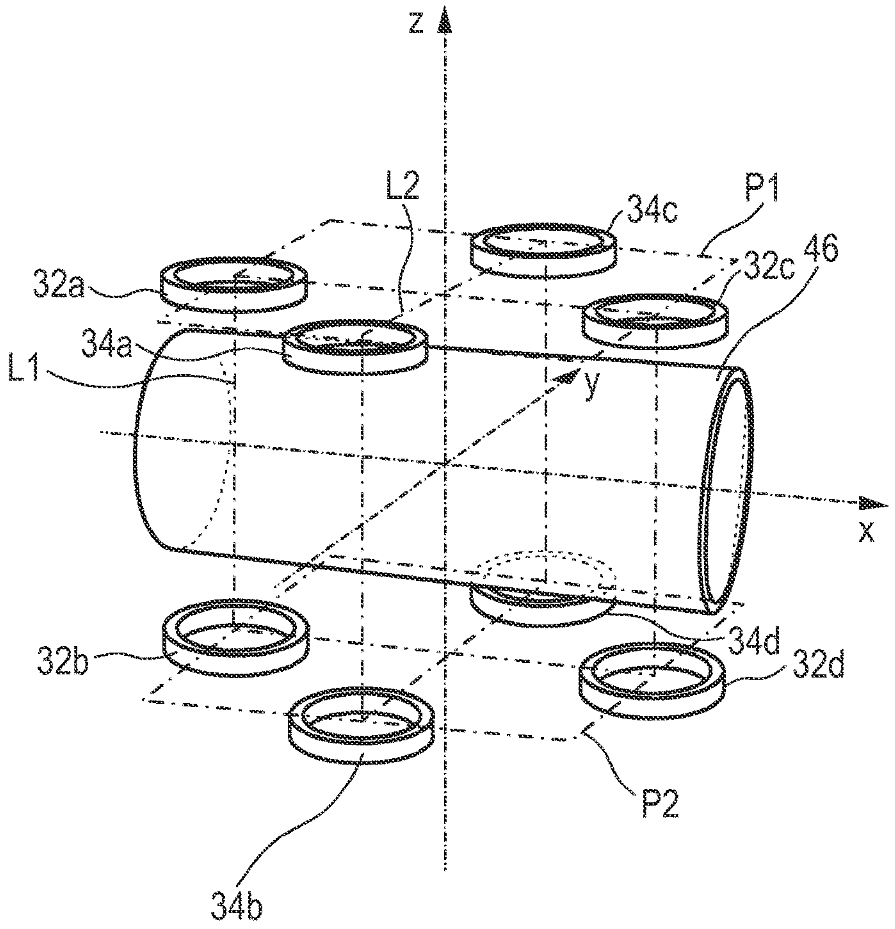

FIG. 6 shows a first embodiment of an apparatus according to the present invention. FIG. 6*a* shows the detailed arrangement of the various coils of the arrangement, FIG. 6*b* shows a diagram indicating the position of the eight focus field coils of two focus field coil subunits provided in this embodiment.

In particular, in this embodiment the two x focus field coils 32 of the conventional MPI apparatus shown in FIG. 3 are replaced by a focus field coil subunit comprising four focus field coils 32*a*, 32*b*, 32*c*, 32*d* as shown in FIG. 5*b*. Further, the two y focus field coils 34 of the conventional MPI apparatus shown in FIG. 3 are replaced by a second focus field coil subunit comprising four focus field coils 34*a*, 34*b*, 34*c*, 34*d*. Preferably, as shown particularly in the diagram of FIG. 6*b*, two focus field coils of each of said tool subunits are arranged in a respective focus field coil plane P1, P2, which are arranged in parallel to each other and parallel to the x-y-plane, i.e. coils 32*a*, 32*c*, 34*a*, 34*c* are arranged in plane P1, and coils 32*b*, 32*d*, 34*b*, 34*d* are arranged in plane P2. Further, the four focus field coils 32*a*-32*d* of the first subunit are all arranged in a first focus field coil layer L1 which is parallel to the x-z-plane, and the four focus field coils 34*a*-34*d* of the second focus field coil subunit are all arranged in a second focus field coil layer L2 which is parallel to the y-z-plane. Said layers L1 and L2 are thus, in this embodiment, arranged perpendicular to each other and perpendicular to the planes P1, P2.

Such a regular arrangement of the focus field coils allows easier mechanical construction and arrangement, and further easier calculation/estimation of the generated magnetic field.

A further advantage of such an arrangement of the focus field coils is that it provides an easier access to a patient, in particular the patient's body portion arranged in the field of view, which can be much more easily accessed from the x direction compared to the conventional arrangement of the MPI apparatus as shown in FIGS. 1 and 3.

In addition to the two focus field coil subunits a third focus field coil subunit may additionally be provided, which may comprise only one pair of focus field coils (not shown). Alternatively, the selection field coils 36 may also be used as third focus field coil subunit as explained above with reference to FIGS. 1 and 3.

Further, to generate the magnetic drive field in the MPI mode additional drive field coils (not shown) may be provided in the conventional manner, and for receiving of detection signals in the MPI mode one or more receive coils are additionally provided (not shown) in the conventional manner.

Still further, for operating the apparatus in the MRI mode, one or more additional RF coils are provided for RF excitation pulses, and receive coils are provided for receiving MRI signals. For these purposes the same coils as conventionally used in an MRI apparatus may be provided. For instance, at low frequencies (low for MRI, e.g. as used in low-field MRI or pre-polarized MRI), the drive field coils can also be used as transmit and receive coils for MRI.

FIGS. 7 and 8 illustrate for the focus field coil subunit 320, just as an example, the generation of different magnetic fields in the MPI mode (FIG. 7) and in the MRI mode (FIG. 8). The four focus field coils 32*a*-32*d* are, as shown in FIGS. 7*a*, 7*c*, 8*a*, 8*c*, arranged in the same way as shown in FIG. 5*b*. However, different currents are provided to the various coils depending on whether the arrangement shall be used in an MPI mode or in an MRI mode. These currents are indicated by arrows in FIGS. 7*a* and 8*a*. Further, in FIGS. 7*a* and 8*a* an area A1 is shown for which the distribution of the magnetic field is shown in FIGS. 7*b* and 8*b*, respectively. In FIGS. 7*c* and 8*c* another, much smaller area A2 is indicated for which the distribution of the magnetic field is shown in FIGS. 7*d* and 8*d*, respectively. Further, in FIGS. 7*e* and 8*e* the dependence of the magnetic field Bx (FIG. 7*e*) and Bx and Bz (FIG. 8*e*) on x at z=0 are shown.

Figure 7A:
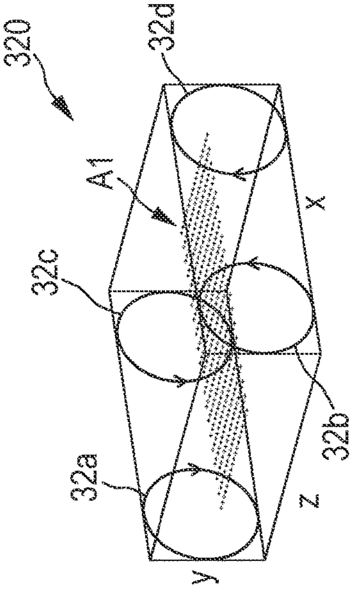
FIG. 7 illustrates the generation of a homogeneous magnetic field in an MPI mode with coils as proposed according to the present invention.
Figure 7B:
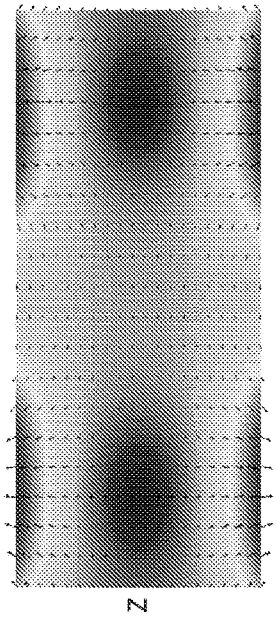
Figure 7C:
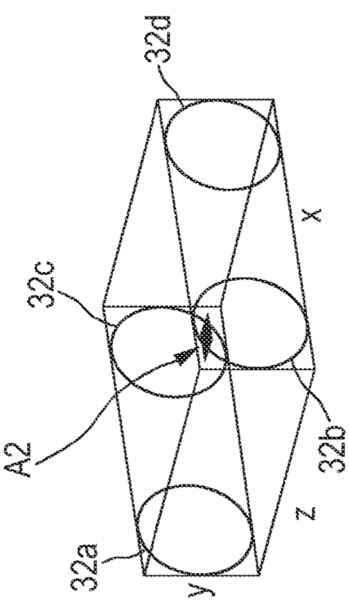
Figure 7D:
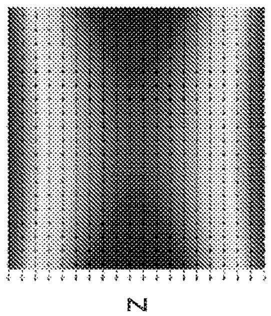
Figure 7E:
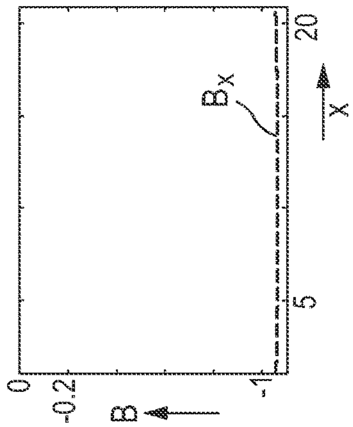

As shown in FIG. 7*a*, for operation of the apparatus in MPI mode, the focus field coils 32*a*, 32*b* and 32*c*, 32*d*, respectively, of each of said two pairs of the focus field coil subunit 320 are provided with focus field currents of opposite directions resulting in a homogeneous magnetic focus field between the focus field coils in x direction, i.e. the Bx magnetic field in the central area of the four focus field coils 32*a*-32*d* is rather homogeneous as shown in FIGS. 7*c* to 7*e*.

Figure 8C:
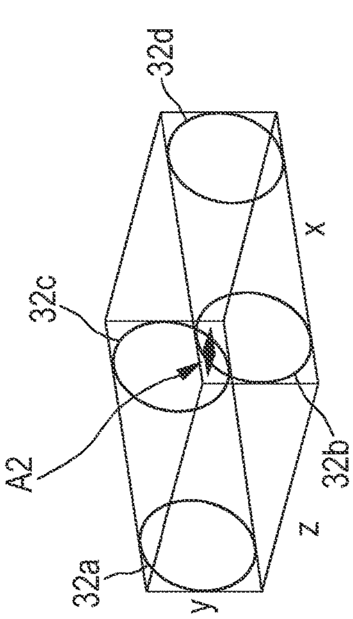
FIG. 8 illustrates the generation of a magnetic gradient field in an MRI mode with coils as proposed according to the present invention.
Figure 8A:
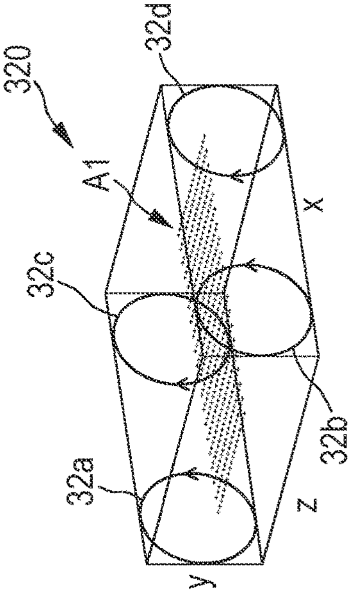
Figure 8D:
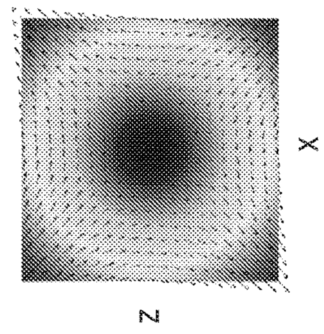
Figure 8E:
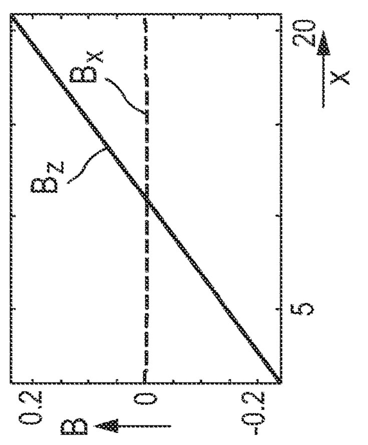
Figure 8B:
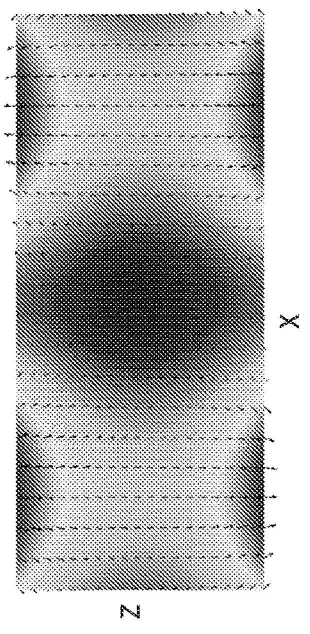

As shown in FIG. 8*a*, for operation of the apparatus in MRI mode, the two focus field coils 32*a*, 32*b* and 32*c*, 32*d*, respectively, of each of said two pairs of the focus field coil subunit 320 are provided with focus field currents of the same direction, wherein the two focus field coils 32*a*, 32*b* of a first pair are provided with focus field currents of the different direction than the two focus field coils 32*c*, 32*d* of the other pair. This results in a gradient magnetic field, in particular in a magnetic field having a constant gradient in the Bz magnetic field along the x direction as shown in FIGS. 8*b*, 8*d* and 8*e*.

In the MPI mode the selection field coils 36 (see FIG. 6*a*) are provided with selection field currents in the generally known manner for generating the desired magnetic selection field, whereas in the MRI mode said selection field coils 36 are provided with homogeneous field currents for generating a homogeneous magnetic field (B0-field) or a pre-polarizing magnetic field (Bp-field) and/or a bias magnetic field depending on the type of MRI mode operation.

Another embodiment of an apparatus 30' according to the present invention is shown in FIG. 9. This embodiment is quite similar to the embodiment shown in FIG. 6*a* and also comprises two focus field coil subunits each comprising four focus field coils 32*e*-32*h* and 34*e*-34*h* replacing the focus field coils 32, 34 of the conventional MPI apparatus as shown in FIG. 3. These eight focus field coils are also substantially arranged at the same positions as the eight focus field coils of the embodiment shown in FIG. 6*a*. However, differently therefrom, the focus field coils are oriented differently, in particular tilted by 90° so that, for the first focus field coil subunit, the focus field coils 32*e* and 32*f* are facing each other and the focus field coils 32*g* and 32*f* are facing each other, and for the second focus field coil subunit, the focus field coils 34*e*, 34*f* are facing each other and the focus field coils 34*g* and 34*h* are facing each other. As a result, the magnetic fields that can be generated by these differently oriented focus field coils are differently oriented compared to the magnetic fields that can be generated with the focus field coils of the embodiment shown in FIG. 6*a*. All in all, however, all necessary magnetic fields for operating the apparatus in an MPI mode and in an MRI mode can also be generated with this embodiment of the apparatus.

Figure 10A:
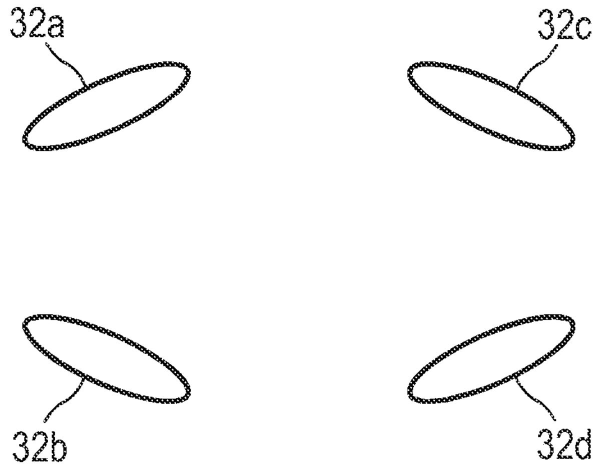
FIG. 10 shows further embodiments for the arrangement of coils as proposed according to the present invention.
Figure 10B:
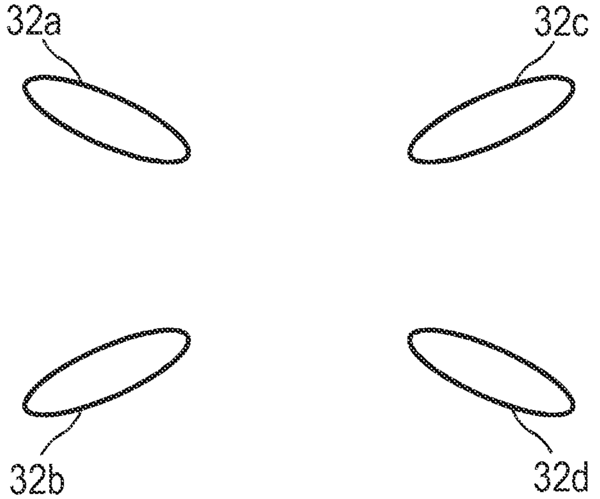

As mentioned above, in the embodiments shown particularly in FIGS. 6-9, the sets of focus field coils replacing the conventionally used pairs of focus field coils are arranged and oriented regularly. However, this is not essential for the present invention. For instance, the four focus field coils of a focus field coil subunit can, as shown in the examples depicted in FIGS. 10*a* and 10*b* for the focus field coils 32*a*-32*d*, be inclined to each other by a certain angle, or they can be displaced with respect to each other so that they are not necessarily all placed in a common plane and/or layer as explained above.

FIG. 11 shows a third embodiment of an apparatus 30" according to the present invention. In this embodiment the focus field coil unit 126 comprises six focus field coils 33*a*-33*f* for generating magnetic focus field components in different directions. These six focus field coils 33*a*-33*f* are grouped into two sets, wherein a first set of three focus field coils 33*a*-33*c* is arranged on a first side of the field of view 28, here above the field of view 28, and a second set of three focus field coils 33*d*-33*f* is arranged on a second side of the field of view 28 opposite said first side, here below the field of view 28. By use of these six focus field coils 33*a*-33*f* similar or almost the same magnetic fields can generally be generated in an MPI mode and an MRI mode as with the eight focus field coils 32*a*-32*d*, 34*a*-34*d* in the embodiment of the apparatus 30 shown in FIG. 6 or as with the eight focus field coils 32*e*-32*h*, 34*e*-34*h* in the embodiment of the apparatus 30' shown in FIG. 9.

Preferably, each set comprises the same number of coils, preferably identical coils, and the coils are arranged as shown in FIG. 11, i.e. respective two coils of different sets are facing each other.

Figure 12A:
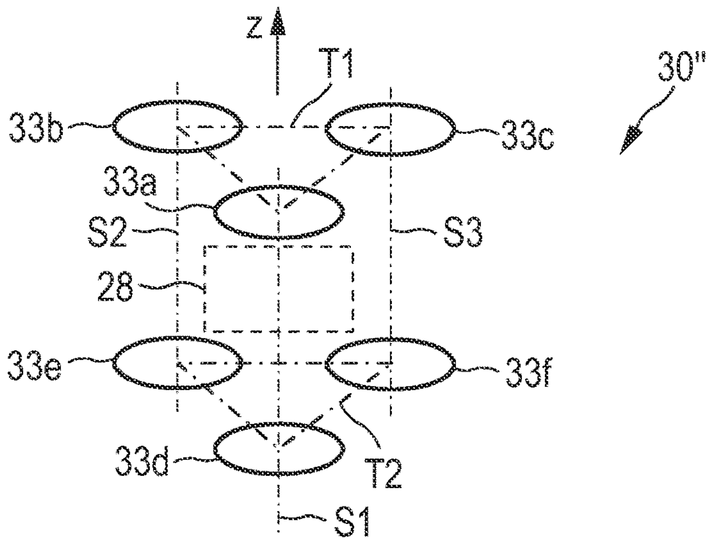
FIG. 12 shows further embodiments for the arrangement of coils as proposed according to the present invention.

FIG. 12 schematically shows some embodiments for the arrangement of the six focus field coils 33*a*-33*f* as proposed according to the present invention. In the embodiment shown in FIG. 12*a* the six focus field coils 33*a*-33*f* are arranged as in the embodiment of the apparatus 30", i.e. the three focus field coils of each set are arranged substantially at the three corners of an equal-sided triangle T1, T2. Further, both triangles T1, T2 of both sets are parallel to each other and equally oriented, i.e. at the same angular position around the z-axis. Still further, the symmetry axes S1, S2, S3 of the three respective pair of two focus field coils 33*a* and 33*d*, 33*b* and 33*e*, 33*c* and 33*f* are parallel to each other and to the z-axis.

Figure 12B:
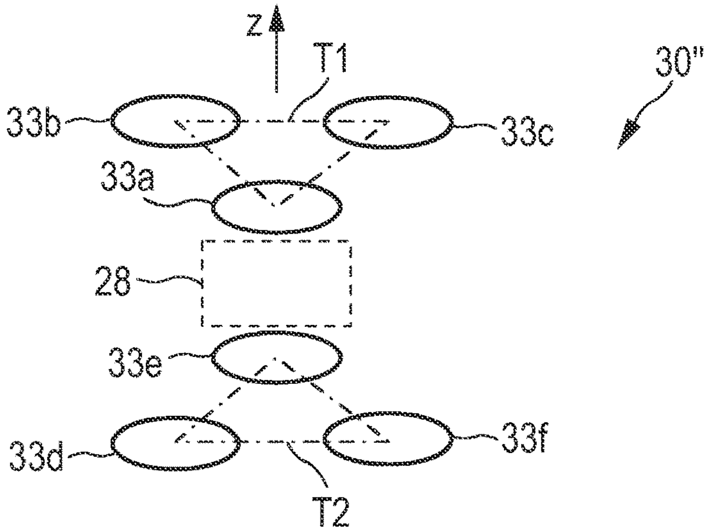

In the embodiment shown in FIG. 12*b* the six focus field coils 33*a*-33*f* are also arranged at the three corners of an equal-sided triangle T1, T2, which are parallel to each other, but the two triangles T1, T2 are oriented differently, i.e. at a different angular position. For instance the two triangles T1, T2 are rotated by 60° (or another angle between 0° and) 120° abound the z-axis.

Figure 13A:
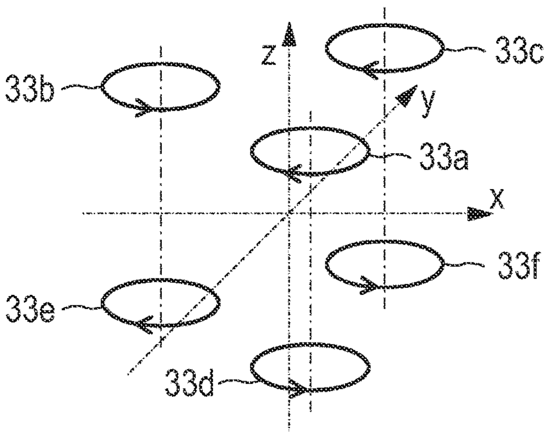
FIGS. 13 to 20 illustrate how the coils of the arrangement shown in FIG. 11 are provided with respective currents in the different modes of operation.
Figure 13B:
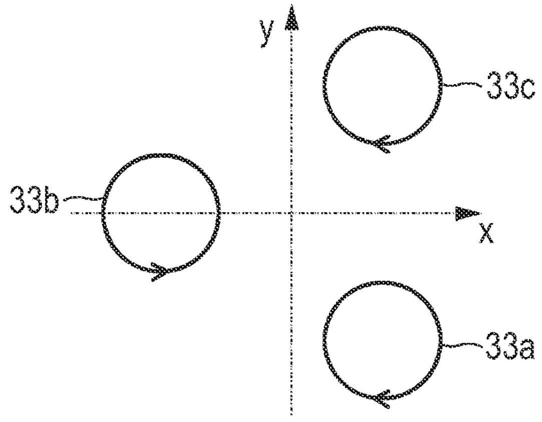
Figure 13C:
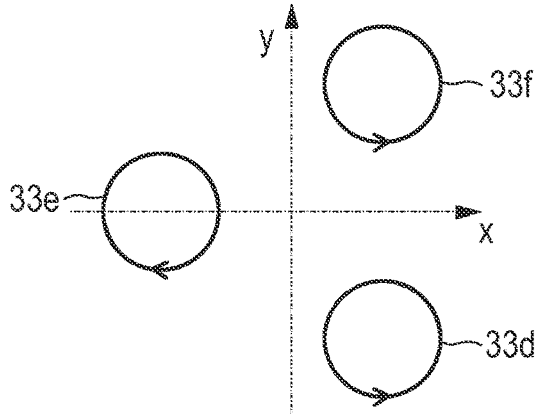
Figure 14A:
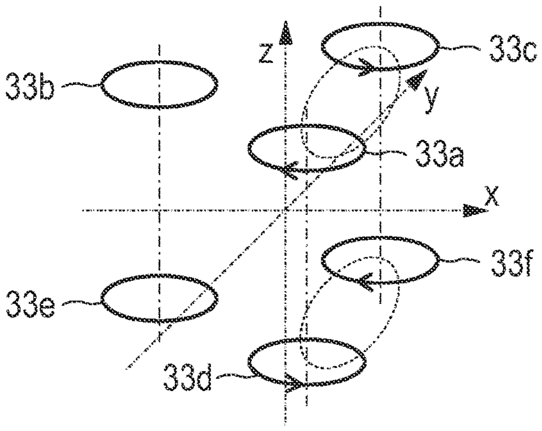
Figure 14B:
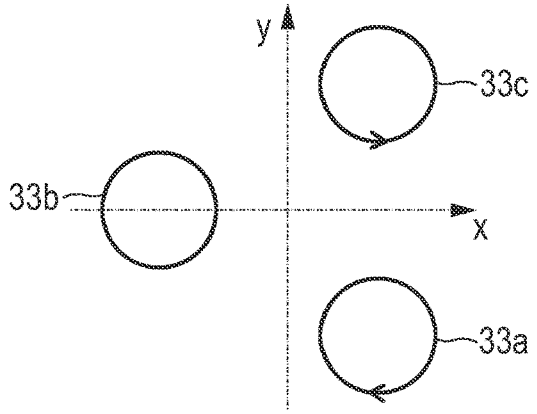
Figure 14C:
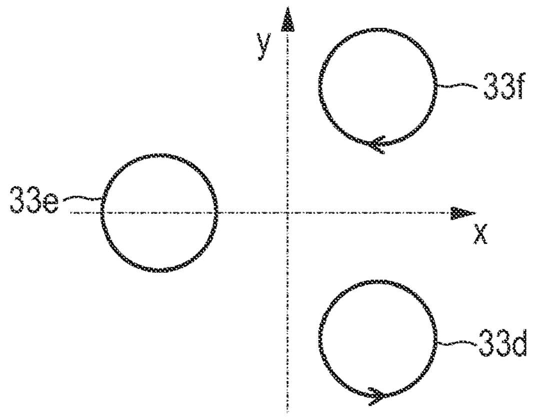
Figure 15A:
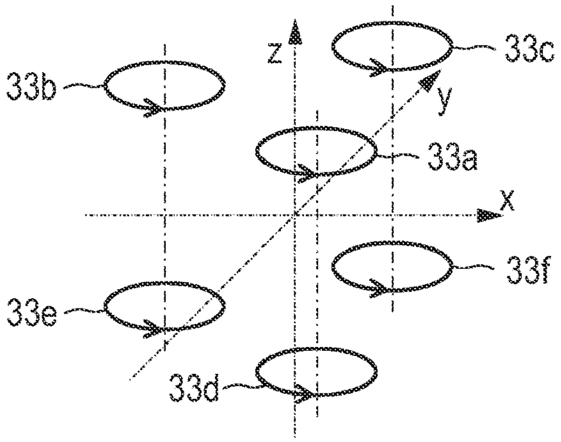
Figure 15B:
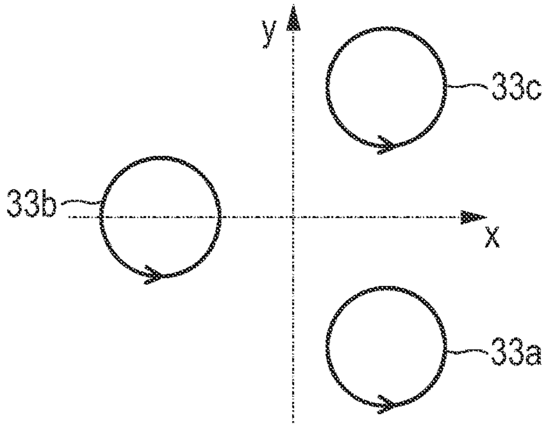
Figure 15C:
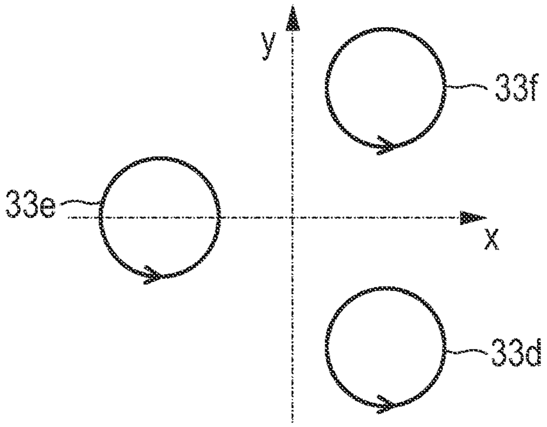
Figure 16A:
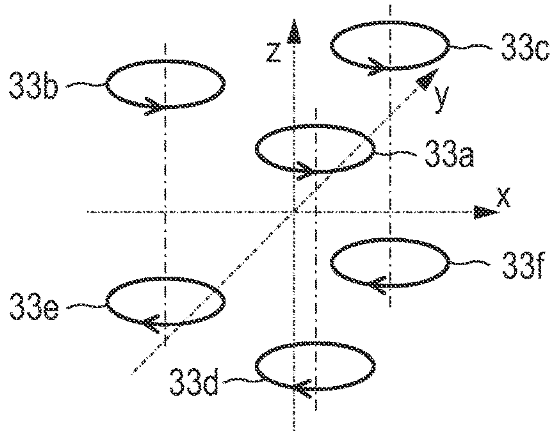
Figure 16B:
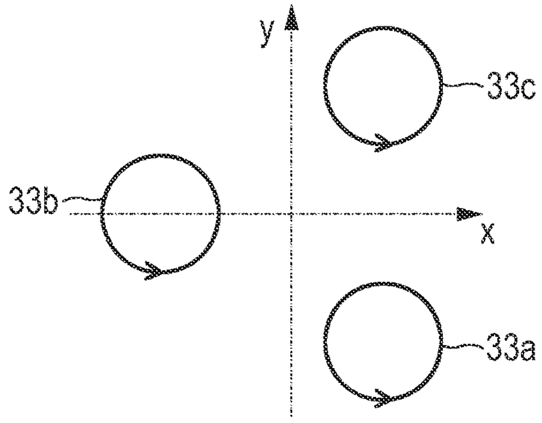
Figure 16C:
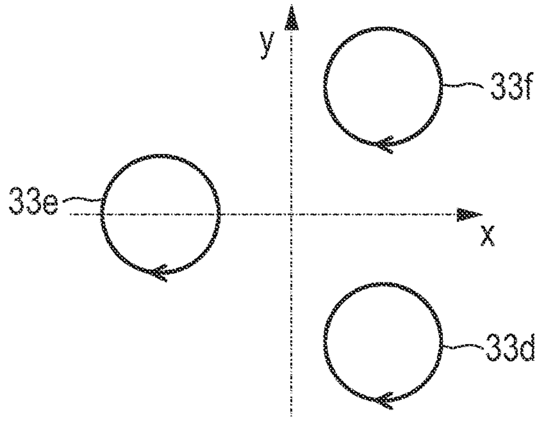
Figure 17A:
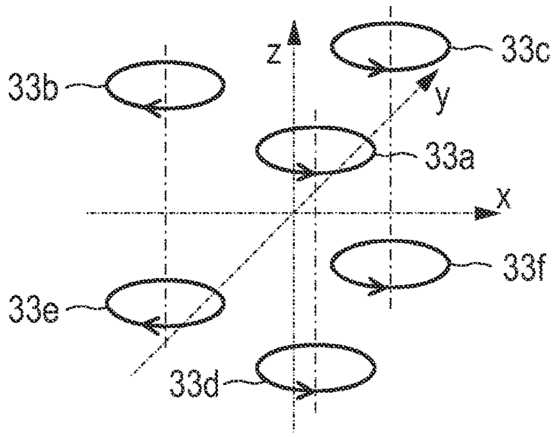
Figure 17B:
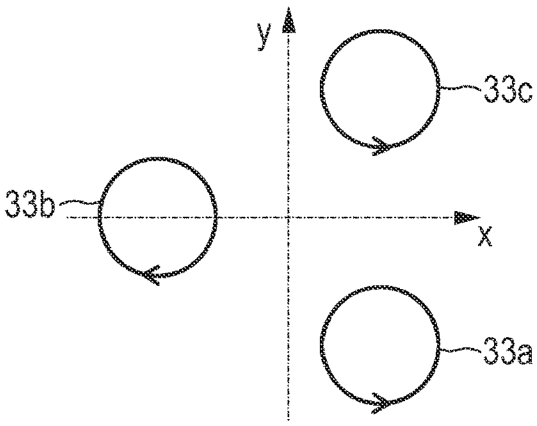
Figure 17C:
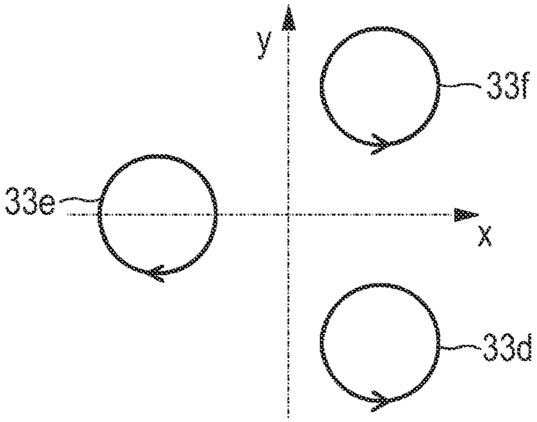
Figure 18A:
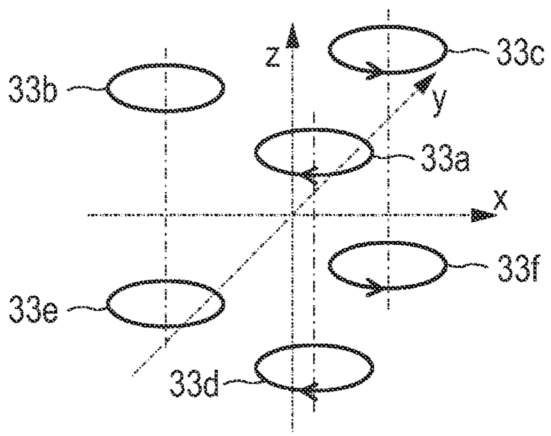
Figure 18B:
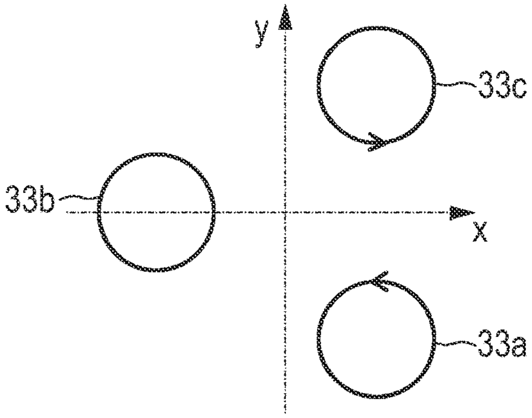
Figure 18C:
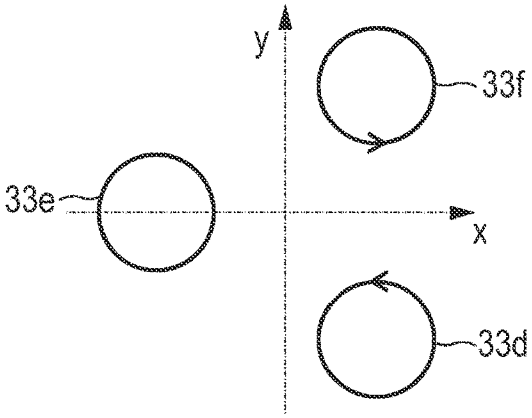
Figure 19A:
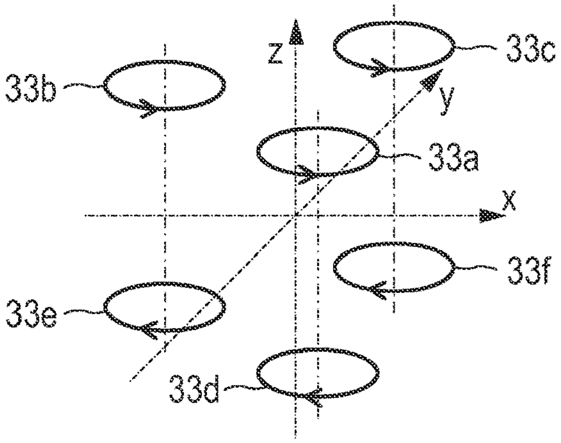
Figure 19B:
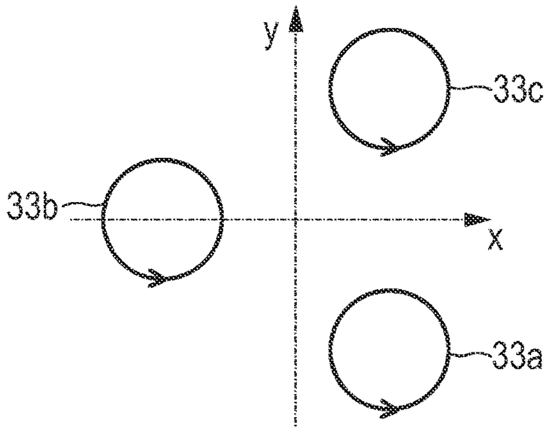
Figure 19C:
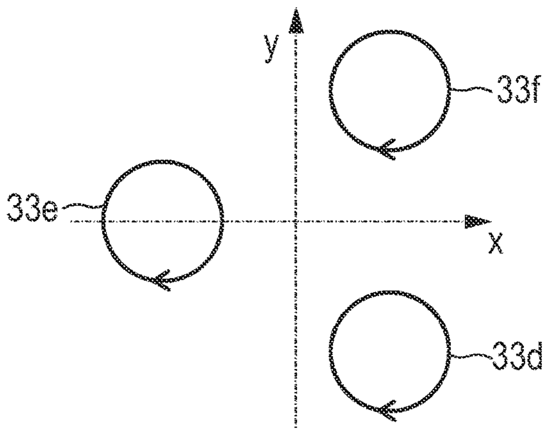
Figure 20A:
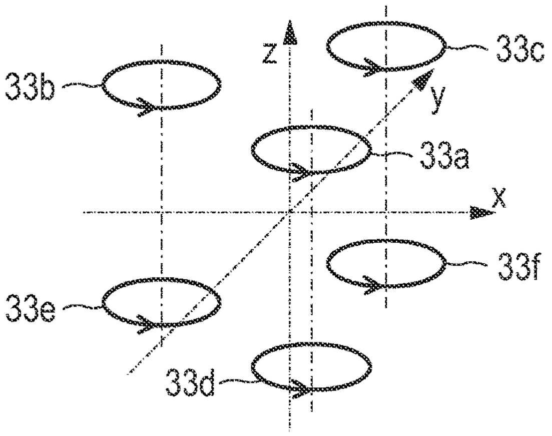
Figure 20B:
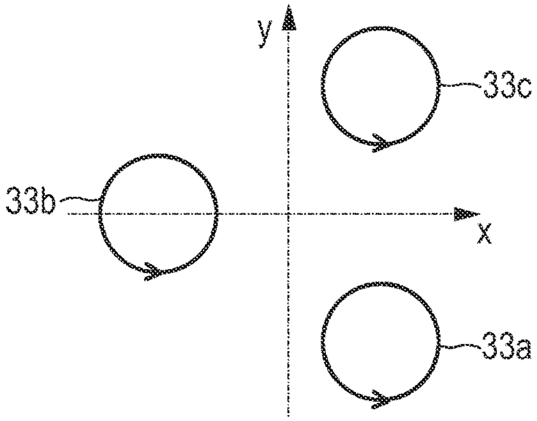
Figure 20C:
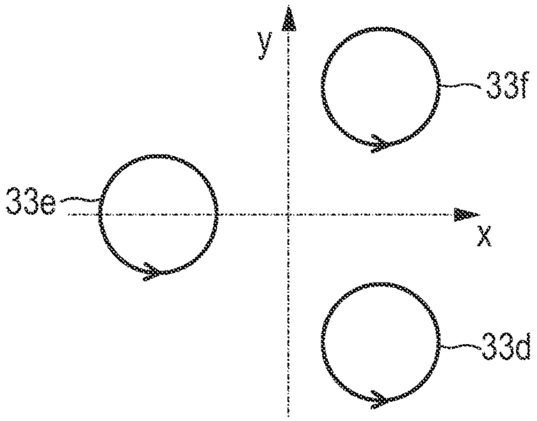

FIGS. 13 to 20 illustrate how the focus field coils 33*a*-33*f* (or, alternatively, in another embodiment, the drive field coils) of the arrangement 30" shown in FIG. 11 and in FIG. 12*a* are provided with respective currents in the different modes of operation. FIG. 13 shows how the focus field coils 33*a*-33*f* are provided with currents (indicated by the arrows) in the MPI mode for generating a substantially homogeneous magnetic focus field $B_x$ in x direction. FIG. 13*a* shows a schematic perspective view, FIG. 13*b* shows a top view of the top coils 33*a*-33*c* and FIG. 13*c* shows a bottom view of the bottom coils 33*d*-33*f*. Similarly, FIG. 14 shows how the focus field coils 33*a*-33*f* are provided with currents in the MPI mode for generating a substantially homogeneous magnetic focus field $B_y$ in y direction. The coils 33*b* and 33*e* are not provided with currents in this example in this mode. FIG. 15 shows how the focus field coils 33*a*-33*f* are provided with currents in the MPI mode for generating a substantially homogeneous magnetic focus field B, in z direction. FIG. 16 shows how the focus field coils 33*a*-33*f* are provided with currents in the MPI mode for generating the selection magnetic field. FIG. 17 shows how the focus field coils 33*a*-33*f* are provided with currents in the MRI mode for generating a magnetic gradient field $G_x$ (=$dB_z/dx$) having a gradient in x direction. FIG. 18 shows how the focus field coils 33*a*-33*f* are provided with currents in the MRI mode for generating a magnetic gradient field $G_y$ (=$dB_z/dy$) having a gradient in y direction. The coils 33*b* and 33*e* are not provided with currents in this example in this mode. FIG. 19 shows how the focus field coils 33*a*-33*f* are provided with currents in the MRI mode for generating a magnetic gradient field $G_z$ (=$dB_z/dz$) having a gradient in z direction. FIG. 20 shows how the focus field coils 33*a*-33*f* are provided with currents in the MRI mode for generating a constant, homogeneous magnetic field $B_0$ in z direction. In the same way as shown in FIG. 13, perspective views (FIGS. 14*a*-20*a*), top views (FIGS. 14*b*-20*b*) and bottom views (FIGS. 14*c*-20*c*) are provided.

In the above, various embodiments of the present invention have been explained in which the conventionally used focus field coils are replaced by focus field coil subunits comprising four focus field coils. In the same way, instead of or in addition to the focus field coils, the drive field coils can be replaced by corresponding drive field coil subunits each comprising four drive field coils. Hence, all explanations provided above with respect to the number, arrangement and orientation of focus field coils are equally applicable to the drive field coils. Thus, in the embodiments shown in FIGS. 5 to 20 instead of or in addition to the focus field coils drive field coils can be provided. Such drive field coils generate, of course, in the MPI mode the magnetic drive fields rather than the magnetic focus fields, but are also operable to generate, in the MRI mode, the required magnetic gradient fields as explained above for the focus field coils. Thus, in such an embodiment said focus field coil unit comprises at least six focus field coils arranged for generating magnetic focus field components in different directions, wherein a first set of at least three focus field coils is arranged on a first side of the field of view and a second set of at least three focus field coils is arranged on a second side of the field of view opposite said first side.

It should be noted here that the drive field is applied at several kHz, whereas gradients may be applied much slower/longer. The current controller should thus generally be able to work at high and low frequencies.

It should further be noted that the number and/or arrangement of is not limited to the above explained and illustrated embodiments. For instance, for the drive field coils and/or the focus field coils arrays of coils may be used which are coupled together as appropriate to generate the desired magnetic fields in the desired mode of operation.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An apparatus configured for operation in a magnetic particle imaging mode that influences and/or detects magnetic particles in a field of view and configured for operation in a magnetic resonance imaging mode, wherein the apparatus comprises:

selection means comprising a selection field signal generator unit and selection field coils which is configured to generate a magnetic selection field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view;

drive means comprising a drive field signal generator unit and drive field coils which changes a position in space of the two sub-zones in the field of view by means of a magnetic drive field so that the magnetization of the magnetic particles changes locally; and focus means comprising a focus field signal generator unit and a focus field coil unit which changes a position in space of a location of the field of view by means of an application of a magnetic focus field allowing the field of view to vary during the magnetic particle imaging mode or the magnetic resonance imaging mode, wherein said focus field coil unit comprises at least six focus field coils that are arranged for generating magnetic focus field components in different directions, wherein a first set of at least three focus field coils is arranged on a first side of the field of view and a second set of at least three focus field coils is arranged on a second side of the field of view opposite said first side.

2. The apparatus as claimed in claim 1, wherein the at least three focus field coils of each set of focus field coils are substantially arranged in order to form a respective focus field coil plane.

3. The apparatus as claimed in claim 1, wherein respective two focus field coils of different sets form a pair of focus field coils having substantially the same symmetry axis, wherein the symmetry axes of the different pairs are arranged substantially in parallel to each other arranged at different positions with respect to the position in space of the field of view.

4. The apparatus as claimed in claim 1, wherein said focus field coil unit comprises at least eight focus field coils, said eight focus field coils being assigned to two focus field coil subunits each focus field coil subunit comprising two pairs of focus field coils, said eight focus field coils of said two focus field coil subunits being arranged on different sides of the field of view, wherein two respective coils of each of the four pairs are substantially facing each other across the field of view.

5. The apparatus as claimed in claim 4, wherein the four focus field coils of each of the two pairs of focus field coils are substantially arranged in a respective focus field coil layer, wherein said two respective focus field coil layers are substantially arranged orthogonal to each other.

6. The apparatus as claimed in claim 5, wherein two respective focus field coils of each of said two focus field coil subunits are arranged in a respective focus field coil plane, and wherein said two respective focus field coil planes are arranged substantially in parallel to each other on different sides of the field of view.

7. The apparatus as claimed in claim 6, wherein said two respective focus field coil planes are arranged perpendicular to said two respective focus field coil layers across the field of view.

8. The apparatus as claimed in claim 4, comprising a third focus field coil subunit comprising one pair of focus field coils, with said two focus field coils of the one pair substantially facing each other.

9. The apparatus as claimed in claim 1, further comprising receiving means comprising:

at least one signal receiving unit and at least one receiving coil which is configured for acquiring detection signals, wherein the detection signals depend on the magnetization in the field of view, and wherein the magnetization is influenced by changes in the position in space of locations of the first and second sub-zones.

10. The apparatus as claimed in claim 4, wherein said focus field coils have a substantially D-shaped form, and wherein the straight arm of respective two focus field coils of different pairs are adjacent to each other.

11. A method of operating an apparatus as claimed in claim 1, comprising acts of:

when operating the apparatus in a magnetic particle imaging mode, providing the selection field coils with selection field currents which generate a magnetic selection field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view;

when operating the apparatus in a magnetic resonance imaging mode, providing two focus field coils of different sets of focus field coils oppositely arranged on different sides of the field of view with gradient field currents of identical directions which generate a gradient magnetic field between the focus field coils, and providing the selection field coils with homogenous field currents which generate either a homogenous stationary magnetic field, or a pre-polarizing magnetic field and a bias magnetic field, wherein the two focus field coils of each set of different sets of focus field coils are substantially arranged in order to form a respective focus field coil plane.

12. An apparatus configured for operation in a magnetic particle imaging mode that influences and/or detects magnetic particles in a field of view and configured for operation in a magnetic resonance imaging mode, wherein the apparatus comprises:

selection means comprising a selection field signal generator unit and selection field elements which is configured to generate a magnetic selection field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view;

drive means comprising a drive field signal generator unit and a drive field coil unit which changes the position in space of the two sub-zones in the field of view by means of a magnetic drive field so that the magnetization of the magnetic particles changes locally, wherein said drive field coil unit comprises at least six drive field coils that are arranged for generating magnetic drive field components in different directions, wherein a first set of at least three drive field coils is arranged on a first side of the field of view and a second set of at least three drive field coils is arranged on a second side of the field of view opposite said first side, and wherein the at least three drive field coils of each set of focus drive field coils are substantially arranged in the a respective focus field coil plane.

13. The apparatus as claimed in claim 12, wherein said drive field coil unit comprises three drive field coil subunits, wherein at least one drive field coil subunit comprises one pair of drive field coils arranged for generating a magnetic drive field component in a first direction, and wherein the other two drive field coil subunits together comprise at least six additional drive field coils that are arranged in pairs and configured for generating magnetic drive field components in two further directions.

14. The method of operating an apparatus as claimed in claim 12, comprising acts of:

when operating the apparatus in a magnetic particle imaging mode, providing two drive field coils of different sets oppositely arranged on different sides of the field of view with drive field currents occurring in opposite directions in order to generate a substantially homogeneous magnetic drive field between the drive field coils, and providing the selection field coils with selection field currents in order to generate said magnetic selection field, when operating the apparatus in a magnetic resonance imaging mode, providing two drive field coils of different sets oppositely arranged on different sides of the field of view with gradient field currents of identical directions generating a gradient magnetic field between the drive field coils, and providing the selection field coils with homogenous field currents when generating either a homogenous stationary magnetic field, or a pre-polarizing magnetic field and a bias magnetic field.

15. A non-transitory computer readable medium comprising computer instructions which, when executed by a processor, configure the processor to perform a method of operating an apparatus, the apparatus being configured for operation in a magnetic particle imaging mode that influences and/or detects magnetic particles in a field of view and configured for operation in a magnetic resonance imaging mode, wherein the apparatus comprises:

selection means comprising a selection field signal generator unit and selection field coils which is configured to generate a magnetic selection field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view;

drive means comprising a drive field signal generator unit and drive field coils which changes a position in space of the two sub-zones in the field of view by means of a magnetic drive field so that the magnetization of the magnetic particles changes locally; and focus means comprising a focus field signal generator unit and a focus field coil unit which changes a position in space of a location of the field of view by means of an application of a magnetic focus field allowing the field of view to vary during the magnetic particle imaging mode or the magnetic resonance imaging mode, wherein said focus field coil unit comprises at least six focus field coils that are arranged for generating magnetic focus field components in different directions, wherein a first set of at least three focus field coils is arranged on a first side of the field of view and a second set of at least three focus field coils is arranged on a second side of the field of view opposite said first side, and wherein the method comprising the acts of:

when operating the apparatus in a magnetic particle imaging mode, providing the selection field coils with selection field currents which generate a magnetic selection field having a pattern in space of its magnetic field strength such that a first sub-zone having a low magnetic field strength where the magnetization of the magnetic particles is not saturated and a second sub-zone having a higher magnetic field strength where the magnetization of the magnetic particles is saturated are formed in the field of view;

when operating the apparatus in a magnetic resonance imaging mode, providing two focus field coils of different sets of focus field coils oppositely arranged on different sides of the field of view with gradient field currents of identical directions which generate a gradient magnetic field between the focus field coils, and providing the selection field coils with homogenous field currents which generate either a homogenous stationary magnetic field or a pre-polarizing magnetic field and a bias magnetic field, wherein the two focus field coils of each set of different sets of focus field coils are substantially arranged in order to form a respective focus field coil plane.

* * * * *